United States Patent
Mikkaichi

(10) Patent No.: US 9,943,216 B2
(45) Date of Patent: Apr. 17, 2018

(54) MUCOUS MEMBRANE LIFTING INSTRUMENT FOR ENDOSCOPE AND ENDOSCOPIC TREATMENT SYSTEM

(71) Applicant: OLYMPUS CORPORATION, Hachioji-shi, Tokyo (JP)

(72) Inventor: Takayasu Mikkaichi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/333,657

(22) Filed: Oct. 25, 2016

(65) Prior Publication Data

US 2017/0035274 A1 Feb. 9, 2017

Related U.S. Application Data

(63) Continuation of application No. PCT/JP2015/062979, filed on Apr. 30, 2015.

(30) Foreign Application Priority Data

May 2, 2014 (JP) ................................ 2014-095379

(51) Int. Cl.
*A61B 1/00* (2006.01)
*A61B 17/00* (2006.01)
(Continued)

(52) U.S. Cl.
CPC ............ *A61B 1/00089* (2013.01); *A61B 1/00* (2013.01); *A61B 1/00087* (2013.01);
(Continued)

(58) Field of Classification Search
CPC ................ A61B 1/00087; A61B 1/018; A61B 2017/00234; A61B 2017/00269;
(Continued)

(56) References Cited

U.S. PATENT DOCUMENTS

| 6,007,546 A | 12/1999 | Snow et al. |
| 2004/0158127 A1* | 8/2004 | Okada ................ A61B 1/012 600/127 |
| 2009/0023987 A1 | 1/2009 | Okada et al. |
| 2012/0157994 A1 | 6/2012 | Weitzner |

FOREIGN PATENT DOCUMENTS

| JP | 2002-045369 A | 2/2002 |
| JP | 2005-253873 A | 9/2005 |

(Continued)

OTHER PUBLICATIONS

Jul. 7, 2015 International Search Report issued in International Patent Application No. PCT/JP2015/062979.

(Continued)

*Primary Examiner* — Timothy J Neal
(74) *Attorney, Agent, or Firm* — Oliff PLC

(57) ABSTRACT

An endoscopic mucous membrane lifting instrument includes: a cap mounted at a distal end of an insertion portion of an endoscope device; a first wire disposed at the cap and configured to be capable of protruding from an outer circumferential portion of the distal end of the insertion portion toward a direction more distal than the insertion portion and in a direction approaching an extension line of a central line of the insertion portion; a second wire disposed at the cap and be capable of protruding from the outer circumferential portion of the insertion portion along the central line of the insertion portion in the distal direction than the insertion portion; and a wire-manipulating portion configured to independently operate the first wire and the second wire.

12 Claims, 18 Drawing Sheets

(51) Int. Cl.
  *A61B 1/018* (2006.01)
  *A61B 17/02* (2006.01)
  *A61B 18/14* (2006.01)
  *A61B 1/04* (2006.01)
  *A61B 1/05* (2006.01)

(52) U.S. Cl.
  CPC ...... *A61B 1/00101* (2013.01); *A61B 1/00133* (2013.01); *A61B 1/018* (2013.01); *A61B 17/00* (2013.01); *A61B 17/00234* (2013.01); *A61B 17/0218* (2013.01); *A61B 18/1482* (2013.01); *A61B 1/00165* (2013.01); *A61B 1/051* (2013.01); *A61B 2017/00269* (2013.01); *A61B 2018/1412* (2013.01)

(58) Field of Classification Search
  CPC ........ A61B 17/320016; A61B 17/0218; A61B 17/00234; A61B 18/14; A61B 2018/1412
  See application file for complete search history.

(56) References Cited

FOREIGN PATENT DOCUMENTS

| | | |
|---|---|---|
| JP | 2008-272133 A | 11/2008 |
| JP | 2009-219743 A | 10/2009 |
| JP | 2012-040108 A | 3/2012 |
| JP | 2013-240538 A | 12/2013 |
| JP | 2014-068817 A | 4/2014 |
| WO | 2006/117937 A1 | 11/2006 |

OTHER PUBLICATIONS

Mar. 29, 2016 Office Action issued in Japanese Patent Application No. 2015-563001.

Nov. 28, 2017 Search Report issued in European Patent Application No. 15785359.9.

* cited by examiner

MUCOUS MEMBRANE LIFTING INSTRUMENT FOR ENDOSCOPE AND ENDOSCOPIC TREATMENT SYSTEM

This application is a continuation application based on a PCT International Application No. PCT/JP2015/062979, filed on Apr. 30, 2015, whose priority is claimed on Japanese Patent Application No. 2014-095379, filed on May 2, 2014. The contents of both the PCT International Application and the Japanese Patent Application are incorporated herein by reference.

BACKGROUND OF THE INVENTION

Field of the Invention

The present invention relates to a mucous membrane lifting instrument for an endoscope and an endoscopic treatment system.

Description of Related Art

Mounting an endoscopic auxiliary tool on a distal end of an insertion portion of an endoscope device to improve a function of an endoscope has been known.

For example, an endoscopic treatment system in which an endoscopic hood acting as an endoscopic auxiliary tool is mounted at a distal end of an insertion portion of an endoscope device is disclosed in Japanese Unexamined Patent Application, First Publication No. 2002-45369. The endoscopic hood disclosed in Japanese Unexamined Patent Application, First Publication No. 2002-45369 is provided with a transparent cap having an approximately cylindrical shape, and an endoscopic mount that detachably fixes the endoscopic hood to the distal end of the insertion portion of the endoscope device and has an approximately cylindrical shape.

A distal end of the endoscopic mount has an endoscopic locking portion that projects toward an inner side thereof. A distal end of the cap has a claw that projects toward an inner side thereof.

When the endoscopic treatment system configured in this way is used, the insertion portion of the endoscope device is pressed into the endoscopic mount up to a position at which the distal end of the insertion portion of the endoscope device abuts the endoscopic locking portion. The endoscopic mount of the endoscopic hood is fixed to the distal end of the insertion portion of the endoscope device in a state in which the distal end of the insertion portion of the endoscope device does not enter the cap.

A distal end opening of the cap of the endoscopic hood disclosed in Japanese Unexamined Patent Application, First Publication No. 2002-45369 is pressed against a mucous membrane in a region serving as a treatment target such as a mucous membrane resection target region. An operator of the endoscopic treatment system disclosed in Japanese Unexamined Patent Application, First Publication No. 2002-45369 pushes out a snare wire in a state in which a distal end of the snare wire protruded from a snare sheath to contact with the claw when this endoscopic treatment system is used. As a result, the snare wire is widened on a circumference along an inner circumferential surface of the distal end of the cap, and is disposed at a bottom of a resection portion at which a mucous membrane swells. Subsequently, the operator pulls the snare wire into the snare sheath, and constricts a root of the resection portion of the mucous membrane. Afterwards, a high-frequency current is conducted through the snare wire, and the mucous membrane can be resected.

Furthermore, endoscopic submucosal dissection (ESD) for introducing a high-frequency knife into a body cavity through a channel formed in an insertion portion of an endoscope device and exfoliating a lesion mucosal portion using this high-frequency knife is known.

First, an operator performing the ESD introduces a syringe needle into a body cavity transendoscopically through the channel of the endoscope device. Subsequently, the operator injects a physiological saline solution into a submucosal layer of the lesion mucosal portion using the syringe needle, and bulges the lesion mucosal portion. Further, the operator mounts a counter electrode plate of the high-frequency knife on a patient. Afterwards, the operator introduces the high-frequency knife having a known needle-like electrode into the body cavity transendoscopically. The operator conducts a current through the electrode, pierces the vicinity of the lesion mucosal portion with the electrode, and moves the electrode along the circumference of the lesion mucosal portion in a transverse direction. Then, the submucosal layer around the lesion mucosal portion is incised.

SUMMARY OF THE INVENTION

According to a first aspect of the present invention, an endoscopic mucous membrane lifting instrument includes: a cap mounted at a distal end of an insertion portion of an endoscope device; a first wire disposed at the cap and configured to be capable of protruding from an outer circumferential portion of the distal end of the insertion portion toward a direction more distal than the insertion portion and in a direction approaching an extension line of a central line of the insertion portion; a second wire disposed at the cap and be capable of protruding from the outer circumferential portion of the insertion portion along the central line of the insertion portion in the distal direction than the insertion portion; and a wire-manipulating portion configured to independently operate the first wire and the second wire.

According to a second aspect of the present invention, in the endoscopic mucous membrane lifting instrument according to the first aspect, the first wire may have a first U-shaped portion formed in a U shape at a distal end, and a first proximal wire portion that is connected with the first U-shaped portion and is connected to the wire-manipulating portion; and the second wire may have a second U-shaped portion formed in a U shape having a larger radius of curvature than that of the first U-shaped portion at a distal end, and a second proximal wire portion that is connected with the second U-shaped portion and is connected to the wire-manipulating portion.

According to a third aspect of the present invention, in the endoscopic mucous membrane lifting instrument according to the first aspect, the cap may have a tubular portion that is mounted at the distal end of the insertion portion of the endoscope device, a first through-hole portion which is formed at an outer wall of the tubular portion to extend in parallel with the central line of the insertion portion and into which the first wire is inserted, and a second through-hole portion which is formed at the outer wall of the tubular portion to extend in parallel with the central line of the insertion portion and into which the second wire is inserted; and the first wire may have a first proximal wire portion that are manipulated by the wire-manipulating portion, and an oblique portion that is obliquely connected with the first proximal wire portion and is inclined to approach the central line of the insertion portion from a distal end of the first through-hole portion when protruding more distally from the distal end of the first through-hole portion.

According to a fourth aspect of the present invention, an endoscopic treatment system includes: the endoscopic mucous membrane lifting instrument according to the first aspect; the endoscope device having the insertion portion, the cap being capable of being mounted at the distal end of the insertion portion; and a treatment tool mounted at the endoscope device and configured to perform treatment on a living tissue via the cap.

According to a fifth aspect of the present invention, in the endoscopic mucous membrane lifting instrument according to the first aspect, a distance between the first wire and the second wire may be increased toward a distal side more distal than the insertion portion, in a state in which the first wire and the second wire protrude from the outer circumferential portion of the insertion portion.

According to a sixth aspect of the present invention, in the endoscopic mucous membrane lifting instrument according to the first aspect, the cap may include a projection portion formed to extend from the distal end of the insertion portion more distal than the insertion portion in the distal direction; and a holder portion disposed at a position more proximal than a distal end of the projection and configured to hold the first wire and the second wire to project from and retract into the cap.

According to a seventh aspect of the present invention, in the endoscopic mucous membrane lifting instrument according to the sixth aspect, the projection portion may include a first projection portion configured to extend from the outer circumferential portion of the distal end of the insertion portion toward the distal direction more distal than the insertion portion; and a second projection portion disposed at a position facing the first projection in a radial direction of the insertion portion and configured to extend from the outer circumferential portion of the distal end of the insertion portion toward the distal direction more distal than the insertion portion; and the holder portion may be disposed at a position between the first projection portion and the second projection portion in a radial direction of the outer circumferential portion of the distal end of the insertion portion.

DETAILED DESCRIPTION OF THE INVENTION

First Embodiment

Figure 1:
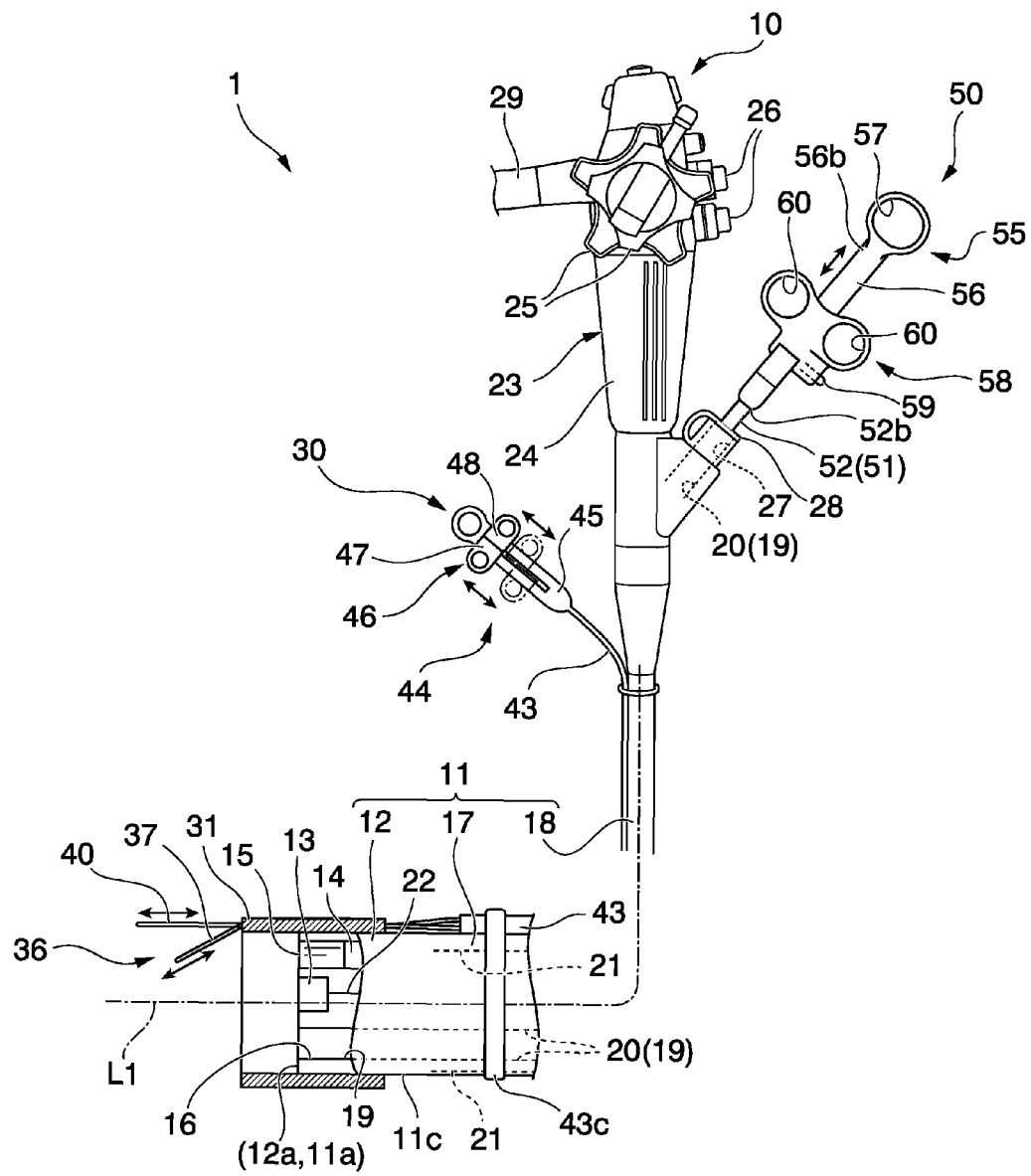
FIG. 1 is an overall view showing an endoscopic treatment system (an endoscopic submucosal dissection (ESD) treatment system) according to a first embodiment of the present invention.
Figure 2:
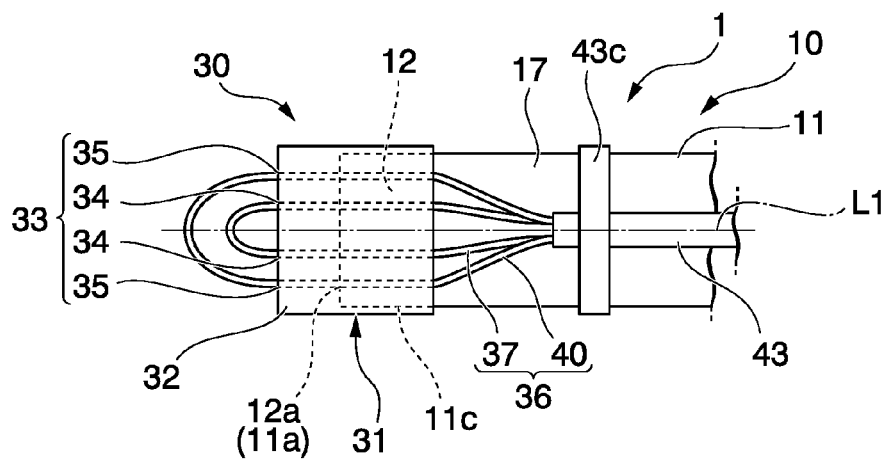
FIG. 2 is a top view of a distal portion in the endoscopic treatment system according to the first embodiment of the present invention.
Figure 3:
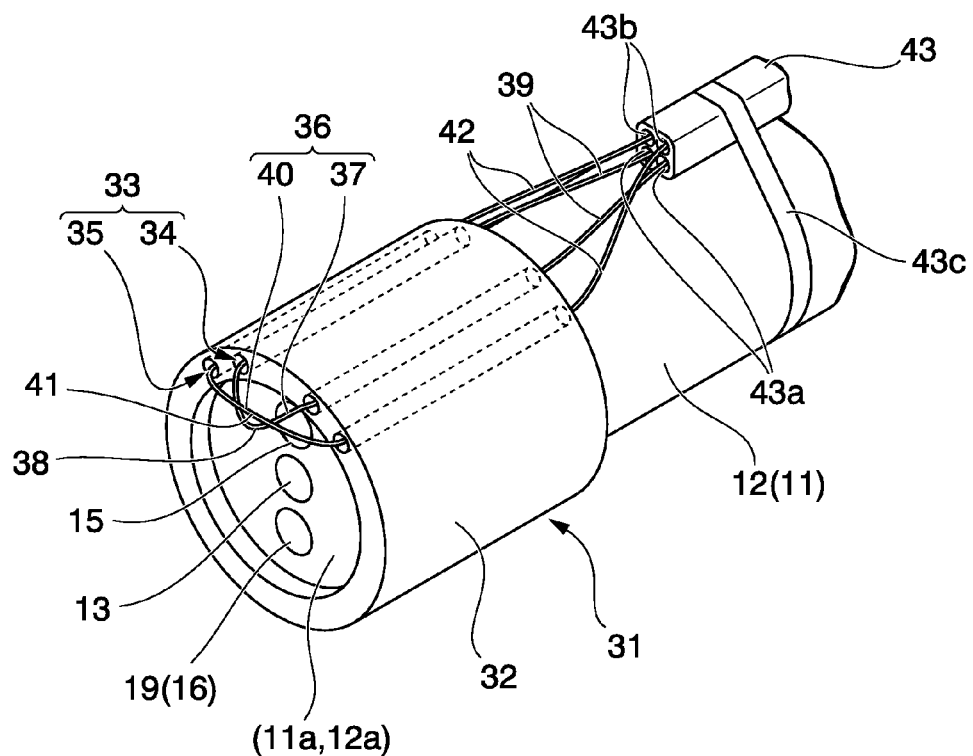
FIG. 3 is a perspective view of the distal portion in the endoscopic treatment system according to the first embodiment of the present invention.
Figure 4:
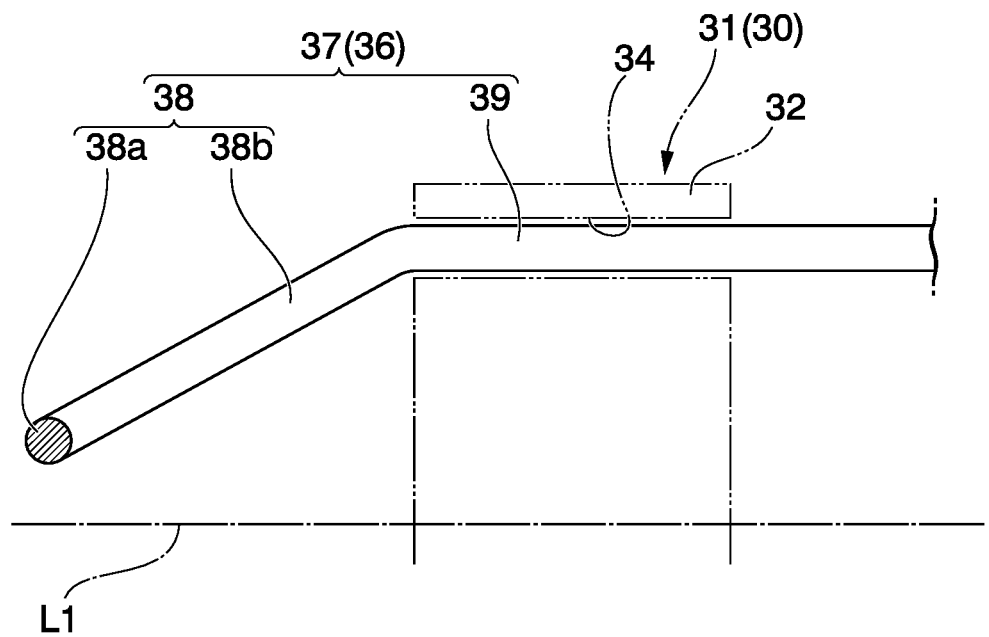
FIG. 4 is a schematic view showing a configuration of a first wire in the endoscopic treatment system according to the first embodiment of the present invention.
Figure 5:
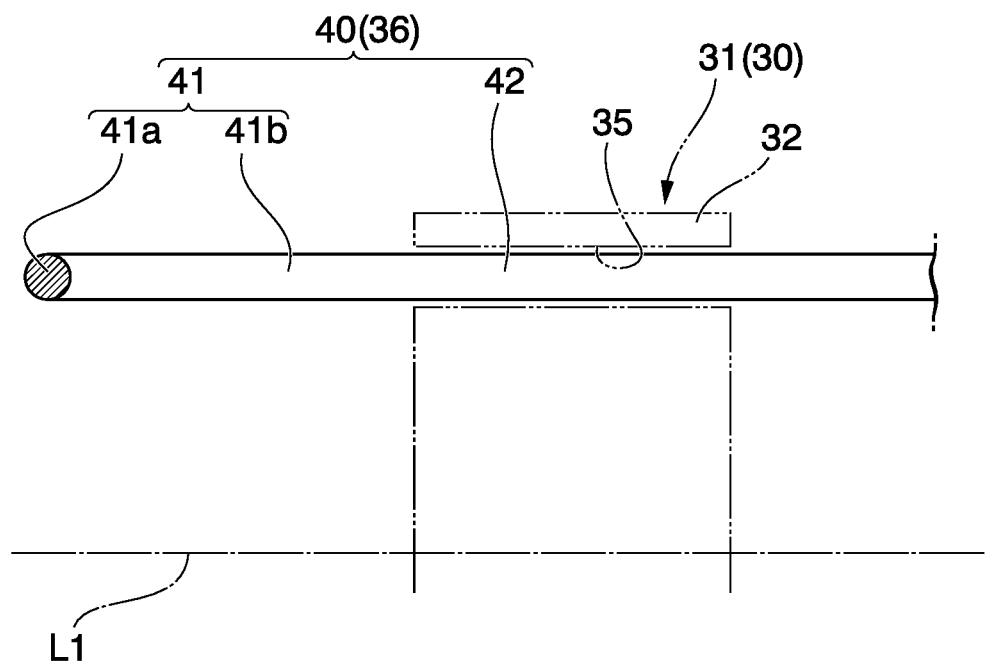
FIG. 5 is a schematic view showing a configuration of a second wire in the endoscopic treatment system according to the first embodiment of the present invention.
Figure 6:
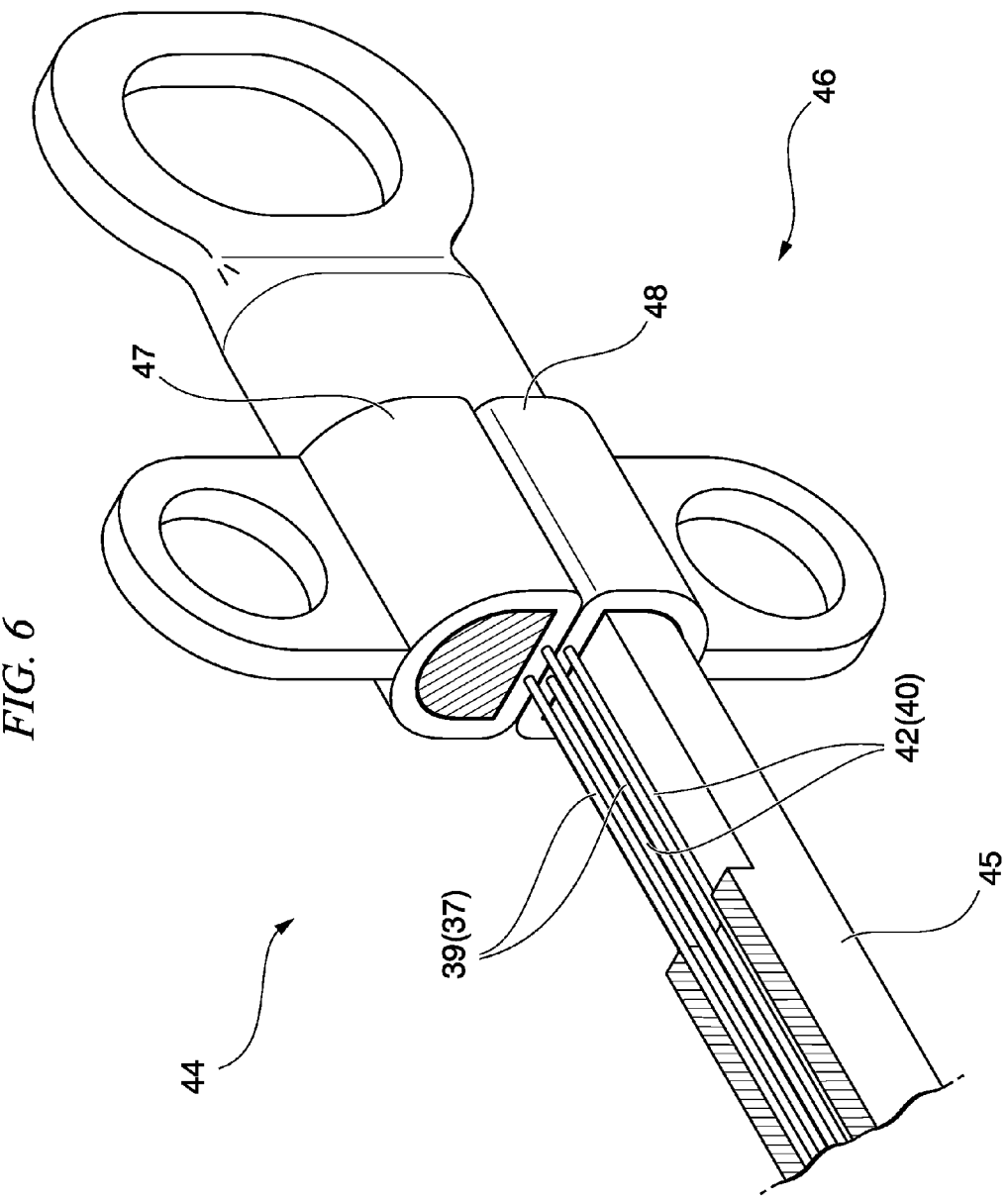
FIG. 6 is a perspective view showing a configuration of a wire-manipulating portion of the endoscopic treatment system according to the first embodiment of the present invention in partial cross section.
Figure 7:
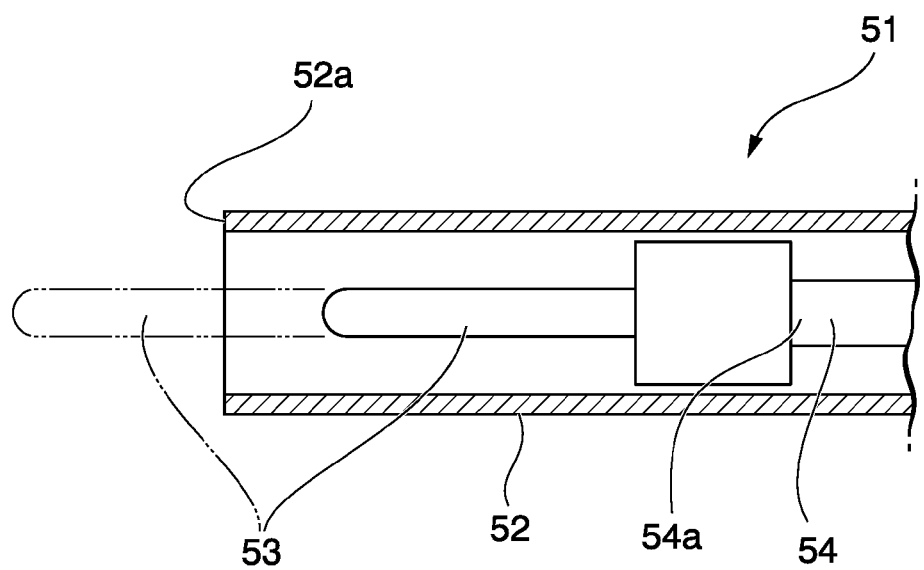
FIG. 7 is a partial cross-sectional view showing a portion of a distal end of an endoscopic treatment tool available along with an endoscope device in the endoscopic treatment system according to the first embodiment of the present invention.

A first embodiment of the present invention will be described. FIG. 1 is an overall view showing an endoscopic treatment system (an endoscopic submucosal dissection (ESD) treatment system) of the present embodiment. FIG. 2 is a top view of a distal portion in the endoscopic treatment system. FIG. 3 is a perspective view of the distal portion in the endoscopic treatment system. FIG. 4 is a schematic view showing a configuration of a first wire in the endoscopic treatment system. FIG. 5 is a schematic view showing a configuration of a second wire in the endoscopic treatment system. FIG. 6 is a perspective view showing a configuration of a wire-manipulating portion of the endoscopic treatment system in partial cross section. FIG. 7 is a partial cross-sectional view showing a portion of a distal end of an endoscopic treatment tool available along with an endoscope device in the endoscopic treatment system.

The ESD treatment system 1 of the present embodiment shown in FIG. 1 is an endoscopic treatment system provided with a configuration suitable to perform the ESD.

As shown in FIG. 1, the ESD treatment system 1 is provided with an endoscope device 10, an endoscopic mucous membrane lifting instrument 30, and an endoscopic resection instrument 50.

The endoscope device 10 is provided with an insertion portion 11, a manipulation portion 23, and a universal cable 29.

The insertion portion 11 is an elongate member that can be inserted into the body.

The insertion portion 11 is provided with a distal rigid portion 12, a bending portion 17, and a flexible tube portion 18.

The distal rigid portion 12 is disposed at a most distal side within the insertion portion 11.

The distal rigid portion 12 has an observation unit 13 for observing a treatment target region, an illumination portion 14 that applies illuminating light to a treatment target region, and a distal opening 16 of a treatment tool channel 19. The distal opening 16 of the treatment tool channel 19 serves as a passage from which an endoscopic treatment tool such as an endoscopic resection instrument 50 protrudes forward.

The observation unit 13 is provided with, for instance, a solid-state image-sensing device such as a charge-coupled device (CCD) area image sensor and an optical system (neither of which is shown). In the present embodiment, the observation unit 13 has a so-called direct-view-type configuration in which an imaging field of view is set in front of the insertion portion 11. The configuration of the observation unit 13 is not particularly limited. That is, an imaging means applicable to a known endoscope may be appropriately selected and applied as an imaging unit.

The illumination portion 14 is provided with an optical fiber that guides illuminating light from an external light source connected via the universal cable 29, and a light-emitting portion 15 that applies light emitted from the light source toward the front of the insertion portion 11 as the illuminating light. The configuration of the illumination portion 14 is not particularly limited. That is, the configuration of the illumination portion 14 may have a configuration in which a light source (not shown) such as a light-emitting diode (LED), a laser diode (LD), or an incandescent lamp is disposed at the distal rigid portion 12 and emits illuminating light.

The distal opening 16 of the treatment tool channel 19 is opened to a distal end face 12a of the distal rigid portion 12. The treatment tool channel 19 is connected up to the manipulation portion 23 through the inside of the distal rigid portion 12, the inside of the bending portion 17, and the inside of the flexible tube portion 18. The treatment tool channel 19 has a proximal opening 27 within the manipulation portion 23. In the present embodiment, the endoscopic treatment tool such as the endoscopic resection instrument 50 can be inserted into the proximal opening 27 of the treatment tool channel 19 via a forceps plug 28 (to be described below).

The bending portion 17 can be bent according to manipulation of an angle knob 25 disposed at the manipulation portion 23.

The flexible tube portion 18 is a tubular member formed of, for instance, a resin. A channel tube 20, an angle wire 21, and a wiring 22 are disposed inside the flexible tube portion 18. The channel tube 20 forms the treatment tool channel 19. The angle wire 21 is provided to transmit a quantity of force for bending the bending portion 17 from the manipulation portion 23. The wiring 22 is provided to transmit electric power or signals for the observation unit 13 and the illumination portion 14.

The manipulation portion 23 is provided with a main body portion 24 which an operator grasps, the angle knob 25 for bending the bending portion 17, a switch set 26 for performing various types of manipulation on the endoscope device 10, and the forceps plug 28 communicating with the proximal opening 27 of the treatment tool channel 19.

Next, a configuration of the endoscopic mucous membrane lifting instrument 30 according to the present embodiment will be described.

As shown in FIGS. 1, 2, and 3, the endoscopic mucous membrane lifting instrument 30 is an instrument that can be attached/detached to/from an outer circumferential surface 11c of a distal end 11a of the insertion portion 11 in the endoscope device 10 of the present embodiment and can be attached to the endoscope device 10 for use to lift a mucous membrane in an ESD procedure.

The endoscopic mucous membrane lifting instrument 30 is provided with a cap 31, an lifting wire 36, a sheath portion 43, and a wire-manipulating portion 44.

The cap 31 is a member that can be attached/detached to/from the distal end 11a of the insertion portion 11 in the endoscope device 10. As shown in FIGS. 2 and 3, the cap 31 is provided with a tubular portion 32 and a first guide portion 33.

The tubular portion 32 is a cylindrical member having an inner diameter that is approximately the same as an outer diameter of the distal end 11a of the insertion portion 11 in the endoscope device 10. The tubular portion 32 can be attached to the distal end 11a of the endoscope device 10 by friction against the outer circumferential surface 11c of the distal end 11a of the endoscope device 10, an adhesive tape (not shown), or the like. In the present embodiment, the central line of the tubular portion 32 is identical to that of the insertion portion 11 in the endoscope device 10. In the present embodiment, the central line of the tubular portion 32 is the central line L1 of the cap 31.

The first guide portion 33 has a first through-hole portion 34 into which a first wire 37 (to be described below) in an lifting wire 36 is inserted, and a second through-hole portion 35 into which a second wire 40 (to be described below) in the lifting wire 36 is inserted.

The first through-hole portion 34 is configured with a pair of through-holes, which are parallel with the central line L1 of the cap 31 and are spaced from each other, formed in an outer wall portion of the cap 31. An inner diameter of each of the through-holes of the first through-hole portion 34 is greater than an outer diameter of the first wire 37 such that the first wire 37 advances and retracts freely.

The second through-hole portion 35 is configured with a pair of through-holes, which are parallel with the central line L1 of the cap 31 and are spaced from each other, formed in an outer wall portion of the cap 31. The first through-hole portion 34 is disposed between the through-holes of the second through-hole portion 35. An inner diameter of each of the through-holes of the second through-hole portion 35 is greater than an outer diameter of the second wire 40 such that the second wire 40 advances and retracts freely.

In the endoscopic mucous membrane lifting instrument 30 according to the present embodiment, the lifting wire 36 is a member that comes into contact with the mucous membrane in order to lift the mucous membrane.

The lifting wire 36 is provided with the first wire 37 and the second wire 40. The first wire 37 and the second wire 40 are preferably formed of a material having a high restoring force to a predetermined shape. For example, the first wire 37 and the second wire 40 are formed of a superelastic alloy, for instance, a NiTi alloy.

As shown in FIGS. 2, 3, and 4, the first wire 37 has a U-shaped portion (a first U-shaped portion 38) and first proximal wire portions 39. The first U-shaped portion 38 is a portion that extends from a distal end side of the cap 31. The first proximal wire portions 39 are connected to the first U-shaped portion 38 and extend to proximal sides of the first U-shaped portion 38.

The first U-shaped portion 38 has a distal portion 38a and oblique portions 38b. The distal portion 38a is a distal end of the first U-shaped portion 38 and has an arc shape in which a wire is folded back 180°. The oblique portions 38b are obliquely connected to the first proximal wire portions 39 in a state in which no external force is applied. In the present embodiment, in the state in which no external force is applied, the oblique portions 38b are bent at a predetermined oblique angle with respect to the first proximal wire portions 39. In a state in which the first wire 37 is installed in the first through-hole portion 34, when the first U-shaped portion 38 is fed out from a distal end of the first through-hole portion 34, the first U-shaped portion 38 is inclined to gradually approach the central line L1 of the cap 31 from a proximal side to a distal side.

The first proximal wire portions 39 are inserted into the first through-hole portion 34 and first sheath portions 43a (to be described below), and extend up to the wire-manipulating portion 44. Proximal ends of the first proximal wire portions 39 are displaced at the wire-manipulating portion 44, and thereby the first U-shaped portion 38 projects/retracts from/into the first through-hole portion 34.

As shown in FIGS. 2, 3, and 5, the second wire 40 has a U-shaped portion (a second U-shaped portion 41) that is a portion extending from the distal end side of the cap 31, and second proximal wire portions 42 that are connected to the second U-shaped portion 41 and extend to proximal sides of the second U-shaped portion 41.

The second U-shaped portion 41 has a distal portion 41a and connecting portions 41b. The distal portion 41a is a distal end of the second U-shaped portion 41 and has an arc shape in which a wire is folded back 180°. The connecting portions 41b are connected to the second proximal wire portions 42.

A radius of curvature of the distal portion 41a in the second U-shaped portion 41 is greater than that of the distal portion 38a of the first U-shaped portion 38.

In the present embodiment, the distal portion 38a of the first U-shaped portion 38 is easily inserted into a relatively small opening, and the distal portion 41a of the second U-shaped portion 41 is formed to easily lift a mucous membrane layer in a wide range.

In the present embodiment, in a state in which no external force is applied, the connecting portions 41b have straight line shapes extending in directions in which the central lines of the second proximal wire portions 42 extend and are connected to the second proximal wire portions 42. In the state in which the second wire 40 is installed in the second through-hole portion 35, when the second U-shaped portion 41 is fed out from a distal end of the second through-hole portion 35, the second U-shaped portion 41 has a shape in which it extends in directions of the central lines of the through-holes of the second through-hole portion 35 and is folded back 180° at the distal side thereof.

The second proximal wire portions 42 are inserted into the second through-hole portion 35 and second sheath portions 43b (to be described below), and extend up to the wire-manipulating portion 44. Proximal ends of the second proximal wire portions 42 are displaced at the wire-manipulating portion 44, and thereby the second U-shaped portion 41 projects/retracts from/into the second through-hole portion 35.

The sheath portion 43 has a pair of first sheath portions 43a into which the first wire 37 is inserted, and a pair of second sheath portions 43b into which the second wire 40 is inserted.

The first sheath portions 43a are a multi-lumen tube corresponding to the two first proximal wire portions 39 in the first wire 37. The first sheath portions 43a are fixed to the tubular portion 32 at positions adjacent to the proximal ends of the through-holes of the first through-hole portion 34 formed at the tubular portion 32.

The second sheath portions 43b are a multi-lumen tube corresponding to the two second proximal wire portions 42 in the second wire 40. The second sheath portions 43b are fixed to the tubular portion 32 at positions adjacent to the proximal ends of the through-holes of the second through-hole portion 35 formed at the tubular portion 32.

In the present embodiment, the first sheath portions 43*a* and the second sheath portions 43*b* are integrally molded as a multi-lumen tube in which four lumens are formed.

The first sheath portions 43*a* and the second sheath portions 43*b* can be connected to the flexible tube portion 18 of the endoscope device, for instance, using a mounting member 43*c* such as a band formed of a resin.

As shown in FIGS. 1 and 6, the wire-manipulating portion 44 has a shaft portion 45 connected to a proximal end of the sheath portion 43, and a slider portion 46 movably mounted at the shaft portion 45.

The shaft portion 45 is a rod-shaped member into which the first wire 37 and the second wire 40 are inserted.

The slider portion 46 has a first slider 47 and a second slider 48. The first slider 47 is fixed to a proximal end of each of the two first proximal wire portions 39 of the first wire 37. The second slider 48 is fixed to a proximal end of each of the two second proximal wire portions 42 of the second wire 40.

The first slider 47 and the second slider 48 can advance and retract relative to the shaft portion 45 independently of each other in a direction of the central line of the shaft portion 45.

When the first slider 47 is displaced to a distal side of the shaft portion 45, the first wire 37 fixed to the first slider 47 is also displaced to the distal side. When the first slider 47 is displaced to a proximal side of the shaft portion 45, the first wire 37 fixed to the first slider 47 is also displaced to the proximal side. The first slider 47 can manipulate projection and retraction of the first wire 37 from and into the first through-hole portion 34 disposed at the tubular portion 32 of the cap 31 shown in FIG. 3.

When the second slider 48 is displaced to the distal side of the shaft portion 45, the second wire 40 fixed to the second slider 48 is also displaced to the distal side. When the second slider 48 is displaced to the proximal side of the shaft portion 45, the second wire 40 fixed to the second slider 48 is also displaced to the proximal side. The second slider 48 can manipulate projection and retraction of the second wire 40 from and into the second through-hole portion 35 disposed at the tubular portion 32 of the cap 31.

A known finger hook structure which an operator can easily manipulate may be provided for the shaft portion 45 and the slider portion 46 as needed.

Next, a configuration of the endoscopic resection instrument 50 mounted at the endoscope device 10 of the present embodiment will be described.

The endoscopic resection instrument 50 shown in FIG. 1 is a treatment tool that resects biological tissue. In the present embodiment, a known endoscopic resection instrument may be suitably selected and applied as the endoscopic resection instrument 50 of the present embodiment. For example, a high-frequency knife, which is supplied with a high-frequency current from a high-frequency power supply to resect biological tissue with cauterization, is applied as the endoscopic resection instrument 50.

As shown in FIGS. 1 and 7, the endoscopic resection instrument 50 (the high-frequency knife 50) of the present embodiment is provided with a treatment tool insertion portion 51, a treatment tool manipulation portion 55, and a counter electrode plate (not shown).

The treatment tool insertion portion 51 is provided with a sheath 52, a resection electrode 53, and a power-supplying wire 54.

The sheath 52 is a tubular member having flexibility, and has an insulating property. The power-supplying wire 54 is disposed inside the sheath 52 to be capable of advancing and retracting.

The resection electrode 53 shown in FIG. 7 is an electrode fixed to a distal end 54*a* of the power-supplying wire 54, and cauterizes and resects biological tissue by coming into contact with the biological tissue while conducting a high-frequency current.

The power-supplying wire 54 is displaced from a distal end 52*a* side to a proximal end 52*b* side of the sheath 52 shown in FIGS. 1 and 7, and thereby the resection electrode 53 is completely housed in the sheath 52 from an opening of the distal end 52*a* of the sheath 52. The power-supplying wire 54 is displaced to the distal end 52*a* side of the sheath 52, and thereby the resection electrode 53 protrudes from the opening of the distal end 52*a* of the sheath 52.

The power-supplying wire 54 is a conductive member for supplying a high-frequency current to the resection electrode 53. The distal end 54*a* of the power-supplying wire 54 is fixed to the resection electrode 53. The proximal end 54*b* of the power-supplying wire 54 is disposed at the treatment tool manipulation portion 55. The proximal end 54*b* of the power-supplying wire 54 is fixed to a slider 58 (to be described below). The power-supplying wire 54 causes the inside of the sheath 52 to project/retract by manipulation of the slider 58.

As shown in FIG. 1, the treatment tool manipulation portion 55 is provided with a rod-shaped manipulation portion body 56 fixed to the proximal end 52*b* of the sheath 52, and the slider 58 provided to be slidable relative to the manipulation portion body 56 in a longitudinal direction of the manipulation portion body 56.

The proximal end 56*b* of the manipulation portion body 56 is provided with a finger-hooking ring 57.

The slider 58 is connected to the manipulation portion body 56 to be able to project/retract in longitudinal direction of the manipulation portion body 56. The slider 58 is provided with a connector 59 fixed to the proximal end 54*b* of the power-supplying wire 54, and finger-hooking rings 60.

The connector 59 provided for the slider 58 is connectable to a high-frequency power supply (not shown). The high-frequency current which the high-frequency power supply emits is conducted from the high-frequency power supply to the resection electrode 53 (see FIG. 7) through the connector 59 (see FIG. 1) and the power-supplying wire 54 (see FIG. 7).

An operator can cause the slider 58 to project/retract from/into the manipulation portion body 56 by putting his/her fingers in the ring 57 provided for the manipulation portion body 56 and the rings 60 provided for the slider 58 and opening/closing his/her hand.

Figure 8:
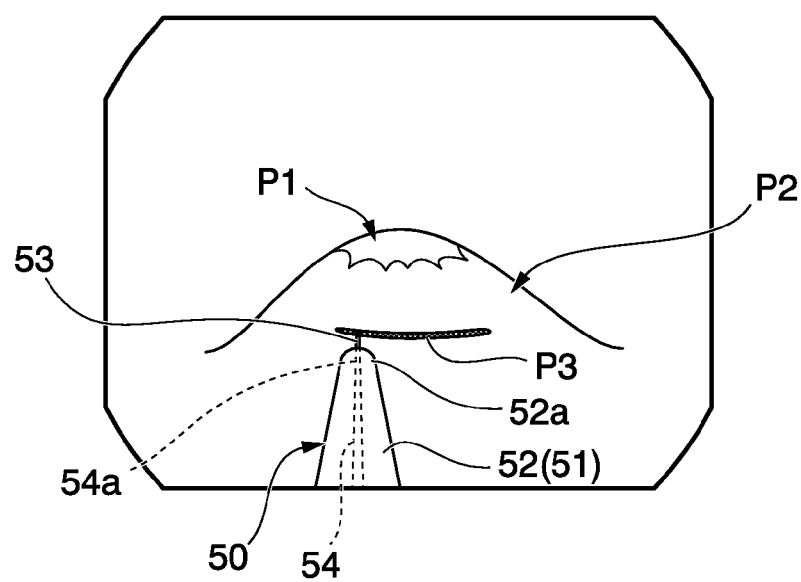
FIG. 8 is a schematic view showing an example of an endoscopic image at the time of using the endoscopic treatment system according to the first embodiment of the present invention.
Figure 9:
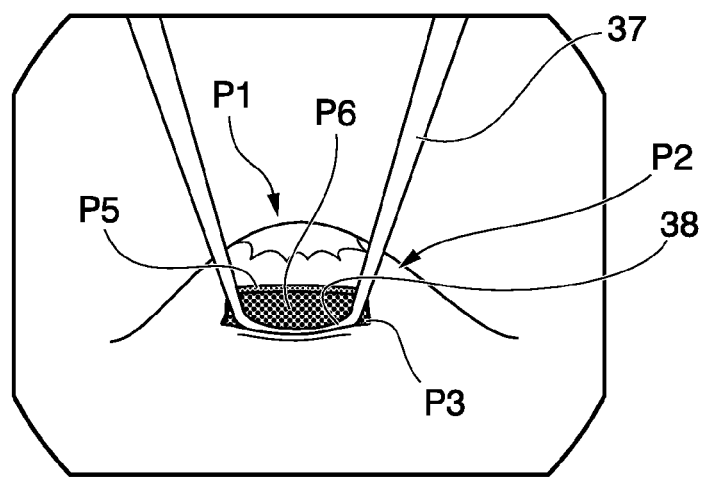
FIG. 9 is a schematic view showing an example of the endoscopic image at the time of using the endoscopic treatment system according to the first embodiment of the present invention.
Figure 10:
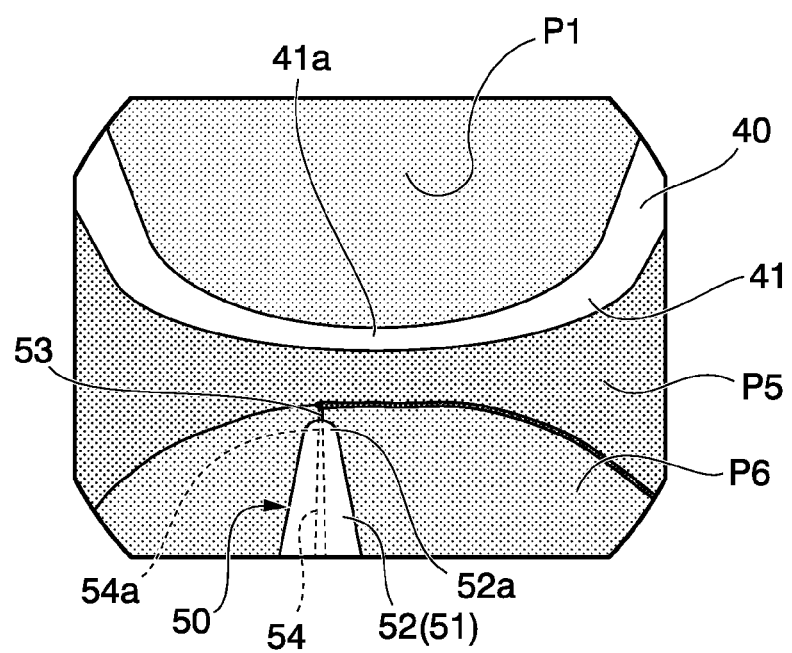
FIG. 10 is a schematic view showing an example of the endoscopic image at the time of using the endoscopic treatment system according to the first embodiment of the present invention.

Next, an operation of the ESD treatment system 1 of the present embodiment will be described. FIGS. 8 to 10 are schematic views showing an example of an endoscopic image when the ESD treatment system 1 (the endoscopic treatment system) is in use.

Hereinafter, an action when a mucous membrane within a body cavity is resected using the ESD treatment system 1 of the present embodiment is given by way of example.

Prior to using the ESD treatment system 1, the counter electrode plate of the high-frequency knife 50 is mounted at a patient. Further, prior to using the ESD treatment system 1, the tubular portion 32 of the endoscopic mucous membrane lifting instrument 30 of the present embodiment is mounted at the distal end 11*a* of the insertion portion 11, and the sheath portion 43 is mounted at the flexible tube portion 18 as needed.

In the state in which the endoscopic mucous membrane lifting instrument 30 is mounted at the ESD treatment system 1 shown in FIG. 1, the first slider 47 and the second slider 48 of the wire-manipulating portion 44 are displaced to the proximal side before the endoscope device 10 is inserted into the body. Thereby, the distal ends of the first and second U-shaped portions 38 and 41 are in proximity with the tubular portion 32 to such an extent that they nearly come into contact with the distal end face of the tubular portion 32 (e.g., see FIG. 3). That is, the first wire 37 and the second wire 40 are stored in the first through-hole portion 34 and the second through-hole portion 35, respectively. The state in which the first and second wires 37 and 40 are respectively stored in the first and second through-hole portions 34 and 35 is a state in which the first and second wires 37 and 40 are withdrawn up to a position at which a field of view according to the endoscope device 10 when viewed via the tubular portion 32 is not obstructed by the first and second wires 37 and 40.

An operator of the ESD treatment system 1 shown in FIG. 1 introduces the distal end 11a of the insertion portion 11 of the endoscope device 10, for instance, from the mouth into the gastrointestinal tract according to a known procedure, and guides the distal end 11a of the insertion portion 11 to the treatment target region. At this point, if necessary, the operator adjusts a position of the distal end 11a of the insertion portion 11 such that a lesion mucosal portion P1 that is a resection target region enters the field of view of the endoscope device 10 while manipulating the angle knob 25 to bend the bending portion 17.

In a state in which the position of the distal end 11a of the insertion portion 11 is held for a patient, the operator introduces a syringe needle (not shown) into the gastrointestinal tract through the forceps plug 28 and the treatment tool channel 19 of the endoscope device 10 shown in FIG. 1. The operator injects a physiological saline solution into a submucosal layer of the lesion mucosal portion P1 using the syringe needle introduced into the gastrointestinal tract, and bulges the lesion mucosal portion P1. After the lesion mucosal portion P1 is bulged, the operator pulls the syringe needle out of the treatment tool channel 19.

Next, as shown in FIG. 1, the operator inserts the high-frequency knife 50 into the treatment tool channel 19. The high-frequency knife 50 is prepared with the resection electrode 53 housed in the sheath 52. The high-frequency knife 50 is prepared in a state in which the connector 59 of the high-frequency knife 50 is connected to the high-frequency power supply.

The operator introduces the treatment tool insertion portion 51 of the high-frequency knife 50 into the treatment tool channel 19 through the forceps plug 28. The operator stops the treatment tool insertion portion 51 at a place where the treatment tool insertion portion 51 protrudes from the distal end 11a of the insertion portion 11.

As shown in FIG. 8, according to the endoscopic image acquired using the observation unit 13 (see FIG. 1) of the endoscope device 10, the state in which the distal end 52a of the sheath 52 is disposed can be visually recognized without being obstructed by the first and second wires 37 and 40.

The operator displaces the slider 58 of the treatment tool manipulation portion 55 shown in FIG. 1 relative to the manipulation portion body 56, and causes the resection electrode 53 shown in FIG. 8 to protrude from the sheath 52 of the high-frequency knife 50. If necessary, the operator bends the bending portion 17 of the endoscope device 10 shown in FIG. 1, and thereby displaces and positions the distal rigid portion 12 of the endoscope device 10 such that a position of the resection electrode 53 reaches a resection-scheduled position. Subsequently, the operator generates the high-frequency current at the high-frequency power supply through a switch manipulation (not shown), and the high-frequency current is conducted through the resection electrode 53 through the connector 59 (see FIG. 1) and the power-supplying wire 54 (see FIG. 8). Further, the operator brings the resection electrode 53, to which the high-frequency current is conducted, into tissue of the resection-scheduled position, and incises the tissue along a predetermined resection scheduled line as shown in FIG. 8.

Accordingly, as shown in FIG. 8, an opening P3 is formed in a mucosal layer P2 of the lesion mucosal portion P1. A size of the opening P3 is not portionicularly restricted. For example, the opening P3 may be formed such that the lesion mucosal portion P1 is incised throughout the circumference thereof by formation of the opening P3. In this case, for the purpose of visually recognizing the resection-scheduled position in the process of forming the opening P3, the endoscopic mucous membrane lifting instrument 30 of the present embodiment may be used.

After the opening P3 is formed, the operator houses the resection electrode 53 in the sheath 52, and pulls the sheath 52 back into the treatment tool channel 19 shown in FIG. 1.

Subsequently, the operator displaces the first slider 47 shown in FIGS. 1 and 6 to the distal side of the wire-manipulating portion 44, and thereby causes the first U-shaped portion 38 of the first wire 37 to protrude from the distal end of the first through-hole portion 34 of the tubular portion 32. As shown in FIGS. 1 and 9, the first U-shaped portion 38 protrudes from the distal end of the tubular portion 32 at an angle inclined with respect to the central line L1 of the cap 31.

The operator displaces the insertion portion 11 of the endoscope device 10 such that the distal end of the first U-shaped portion 38 is inserted into the opening P3 (see FIG. 9).

Thereby, the first U-shaped portion 38 is introduced from the distal end thereof between a submucosal layer P5 and a muscular layer P6. At this point, the submucosal layer P5 is displaced relative to the muscular layer P6 such that, as the first U-shaped portion 38 is inserted into the opening P3, the submucosal layer P5 is gradually spaced from the muscular layer P6. Thereby, a portion between the submucosal layer P5 and the muscular layer P6 can be adequately observed by the endoscope device 10 (see FIG. 1). When the portion between the submucosal layer P5 and the muscular layer P6 is adequately observed by the endoscope device 10, an incision-scheduled position of the mucosal layer P2 for resecting the lesion mucosal portion P1 can be easily seen. The operator performs incision along the incision-scheduled position at a position at which the incision-scheduled position can be seen well while grasping the incision-scheduled position from a gap between the submucosal layer P5 and the muscular layer P6 on the basis of an endoscopic image. Further, the operator displaces the endoscopic mucous membrane lifting instrument 30 to a place where a scheduled position to be incised next can be seen well in the gap between the submucosal layer P5 and the muscular layer P6, and incises the mucosal layer P2. The operator repeats the incision of the mucosal layer P2 and the displacement of the endoscopic mucous membrane lifting instrument 30 to gradually widen the opening P3, thereby making the opening P3 large and deep.

When the first U-shaped portion 38 is further inserted from the opening P3, the tubular portion 32 of the cap 31 is inserted into the opening P3. After the tubular portion 32 of the cap 31 is inserted into the opening P3, the operator also displaces the second slider 48 shown in FIG. 6 to the distal side of the wire-manipulating portion 44 and, as shown in FIG. 10, causes the second wire 40 to protrude from the second through-hole portion 35 to the distal side of the tubular portion 32. The second U-shaped portion 41 of the second wire 40 moves toward the distal side in a direction parallel with the central line of the tubular portion 32 (the central line L1 of the cap 31, see FIG. 1), and thus the submucosal layer P5 pressed by the first U-shaped portion 38 is displaced to be further spaced from the muscular layer P6. Thereby, a greater space is generated between the submucosal layer P5 and the muscular layer P6. If necessary, the operator may pull the first U-shaped portion 38 back to the proximal side, and displace the first wire 37 obstructing the field of view of the endoscope device 10 to the outside of the field of view of the endoscope device 10. As shown in FIG. 10, in the state in which the space between the submucosal layer P5 and the muscular layer P6 is generated by the second U-shaped portion 41, the operator causes the high-frequency knife 50 to protrude from the treatment tool channel 19 again (see FIG. 1). The operator causes the resection electrode 53 to protrude from the sheath 52, and then conducts the high-frequency current to the resection electrode 53 to resect the lesion mucosal portion P1.

After the resection of the lesion mucosal portion P1 is completed, the operator extracts the high-frequency knife 50 and the endoscope device 10 from the gastrointestinal tract. The endoscopic mucous membrane lifting instrument 30 mounted at the insertion portion 11 of the endoscope device 10 is extracted from the gastrointestinal tract along with the endoscope device 10 due to the extraction of the endoscope device 10.

As described above, the endoscopic mucous membrane lifting instrument 30 of the ESD treatment system 1 according to the present embodiment allows the distal end of the first U-shaped portion 38 to be easily inserted into the opening P3 formed in the mucosal layer P2, by the first wire 37 having the first U-shaped portion 38 that obliquely extends from the outer wall portion of the tubular portion 32 to be directed to the central line L1 of the cap 31. That is, the first U-shaped portion 38 obliquely protrudes from the outer circumferential surface of the distal end 11a of the insertion portion 11 toward the central line of the insertion portion 11 in a state in which the endoscopic mucous membrane lifting instrument 30 is mounted at the distal end 11a of the insertion portion 11 of the endoscope device 10, and can be inserted into the opening P3 in the vicinity of the center of the field of view of the endoscope device 10.

Since the second U-shaped portion 41 having a greater radius of curvature than the first U-shaped portion 38 is provided for the endoscopic mucous membrane lifting instrument 30, the submucosal layer P5 is spaced from the muscular layer P6 by the first U-shaped portion 38 and, in this state, the submucosal layer P5 can be displaced by the second U-shaped portion 41, and thereby the submucosal layer P5 is spaced from the muscular layer P6 in a wider area.

In this way, with the endoscopic mucous membrane lifting instrument 30 of the ESD treatment system 1 according to the present embodiment, the cap 31 can be easily inserted between the submucosal layer P5 and the muscular layer P6 through the opening P3 formed in the mucosal layer P2, and furthermore a sufficiently wide operation site (working space) can be created between the submucosal layer P5 and the muscular layer P6 in order to remove the lesion mucosal portion P1.

Although an embodiment of the present invention has been described above in detail with reference to the drawings, the specific configuration is not limited to this embodiment, but also includes changes in design and the like without deportioning from the scope of the present invention.

Modifications of the above-mentioned embodiment are given below.

(First Modification)

Figure 11A:
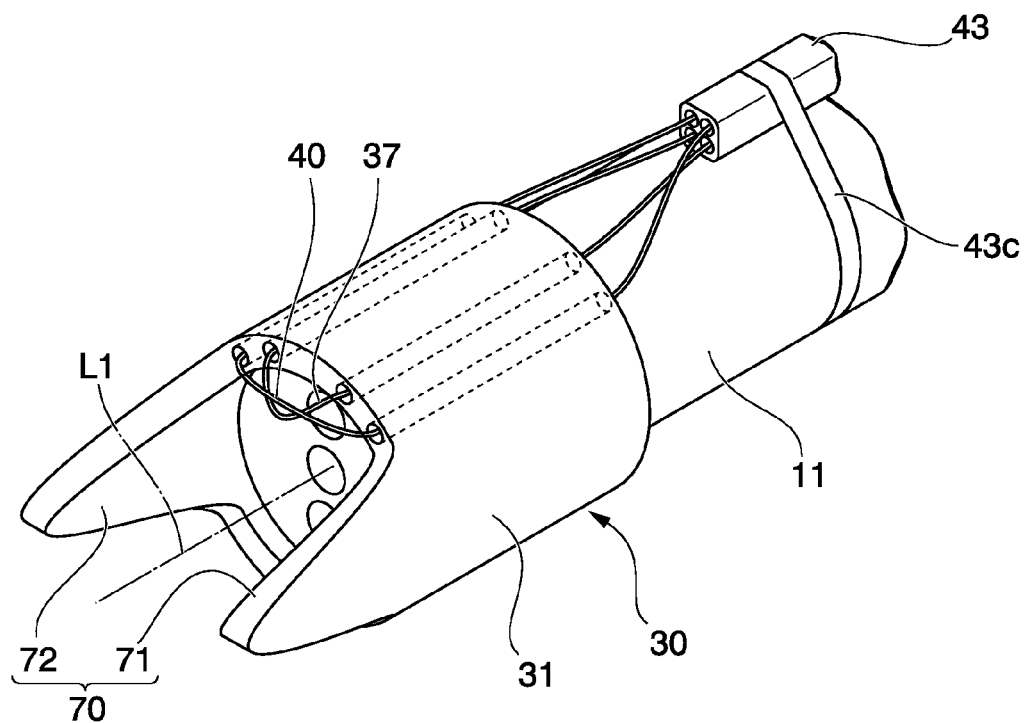
FIG. 11A is a perspective view showing a configuration of a first modification of the first embodiment of the present invention.
Figure 11B:
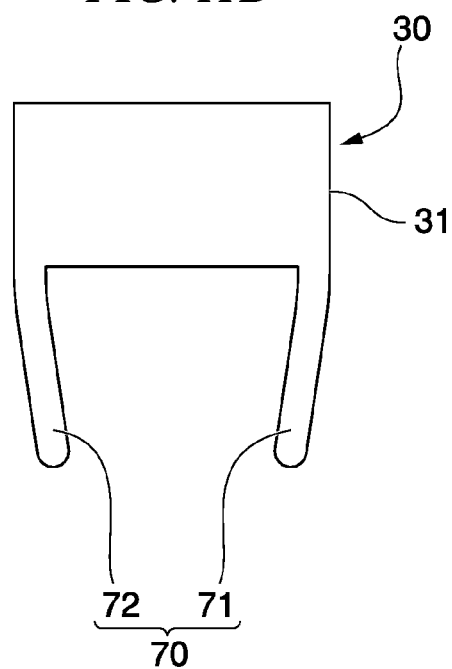
FIG. 11B is a top view showing the configuration of the first modification of the first embodiment of the present invention.
Figure 11C:
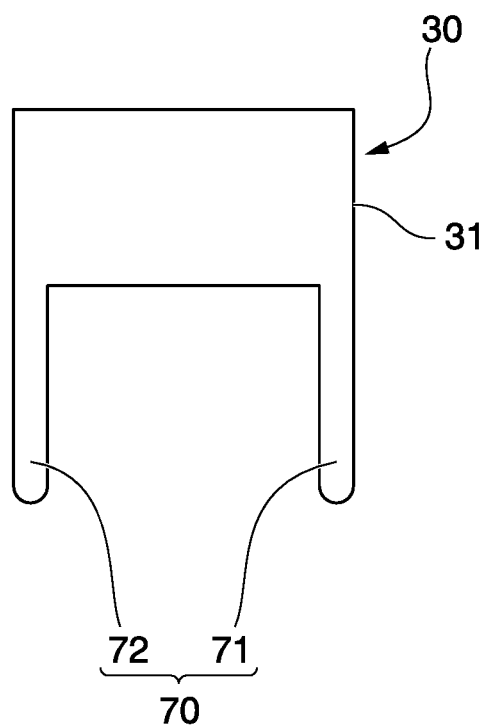
FIG. 11C is a top view showing the configuration of the first modification of the first embodiment of the present invention.

A first modification of the above-mentioned embodiment will be described. FIG. 11A is a perspective view showing a configuration of the present modification. FIG. 11B is a top view showing the configuration of the present modification. FIG. 11C is a top view showing the configuration of the present modification.

As shown in FIG. 11A, in the present modification, a pair of projections 70 provided to further extend from a distal end of a cap 31 to a distal side are provided for the cap 31.

The pair of projections 70 include a first projection 71 and a second projection 72 that are disposed a portion from each other with the central line L1 of the cap 31 located therebetween. Both the first projection 71 and the second projection 72 are formed to be gradually narrowed toward the distal side.

The configuration in which the pair of projections 70 are provided is not essential.

The pair of projections 70 may be configured with distal sides of the pair of projections 70 bent inward in a radial direction of an insertion portion 11 of the endoscope device 10 as shown in FIG. 11B, or angles of distal ends of the pair of projections 70 made round as shown in FIG. 11C to limit invasiveness into tissue of a patient when an endoscope device 10 is inserted.

In the present modification, distal ends of the first and second projections 71 and 72 in the pair of projections 70 can be inserted between a submucosal layer P5 and a muscular layer P6 (see FIG. 10). Thus, the first and second projections 71 and 72 can push the submucosal layer P5 up against the muscular layer P6. As a result, in the present modification, when an lifting wire 36 disposed between the submucosal layer P5 and the muscular layer P6 is pressed and bent against the submucosal layer P5 or the muscular layer P6, the first and second projections 71 and 72 can support the submucosal layer P5 with respect to the muscular layer P6 such that the submucosal layer P5 and the muscular layer P6 are separated.

In the present modification, since the first U-shaped portion 38 prevents the submucosal layer P5 from sagging and entering between the first projection 71 and the second projection 72, the submucosal layer P5 enters between the first projection 71 and the second projection 72 such that the field of view can be prevented from being obstructed.

(Second Modification)

Figure 12:
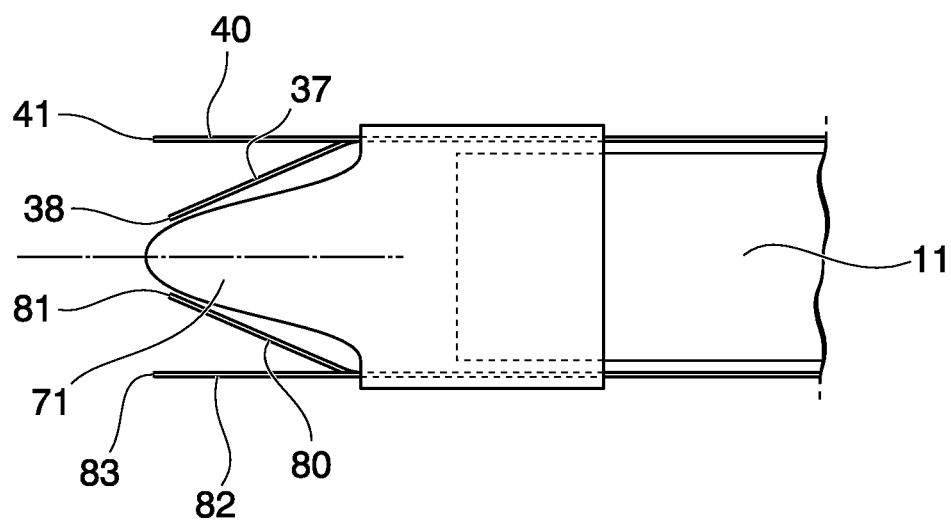
FIG. 12 is a side view showing a configuration of a second modification of the first embodiment of the present invention.

A second modification of the above-mentioned embodiment will be described. FIG. 12 is a side view showing a configuration of the present modification.

As shown in FIG. 12, in the present modification, a third wire 80 and a fourth wire 82, which have the same shapes as a first wire 37 and a second wire 40, are disposed at positions opposite to the first wire 37 and the second wire 40 in a radial direction of a cap 31. Second guide portions 84 (not shown) for guiding the third wire 80 and the fourth wire 82 are formed in the cap 31. The third wire 80 and the fourth wire 82 are preferably formed of a material having a high restoring force to a predetermined shape, like the first wire 37 and the second wire 40. For example, the third wire 80 and the fourth wire 82 are formed of a superelastic alloy, for instance, a NiTi alloy.

The second guide portion 84 is symmetric to the first guide portion 33 of the above-mentioned embodiment with respect to the central line L1 of the cap 31.

Further, a wire-manipulating portion 44 has sliders for manipulating the third wire 80 and the fourth wire 82.

The third wire 80 is symmetric to the first wire 37 with respect to the central line L1 of the cap 31. The third wire 80 has a U-shaped portion (a third U-shaped portion 81) having the same shape as the first U-shaped portion 38 of the first wire 37.

The fourth wire 82 is symmetric to the second wire 40 with respect to the central line L1 of the cap 31. The fourth wire 82 has a U-shaped portion (a fourth U-shaped portion 83) having the same shape as the second U-shaped portion 41 of the second wire 40.

Figure 13:
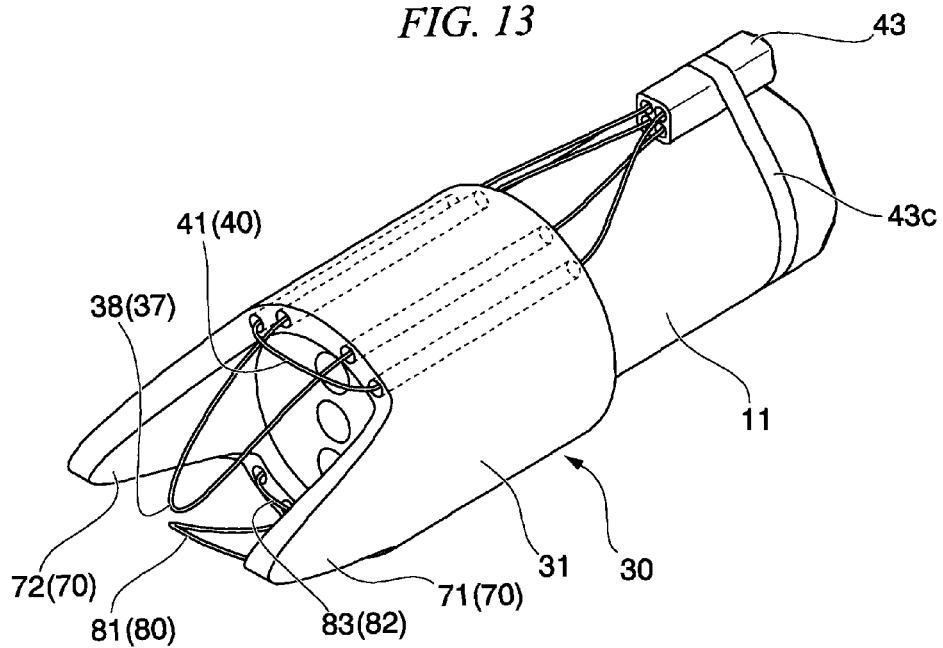
FIG. 13 is a perspective view showing operations of first and third wires in the second modification of the first embodiment of the present invention.
Figure 14:
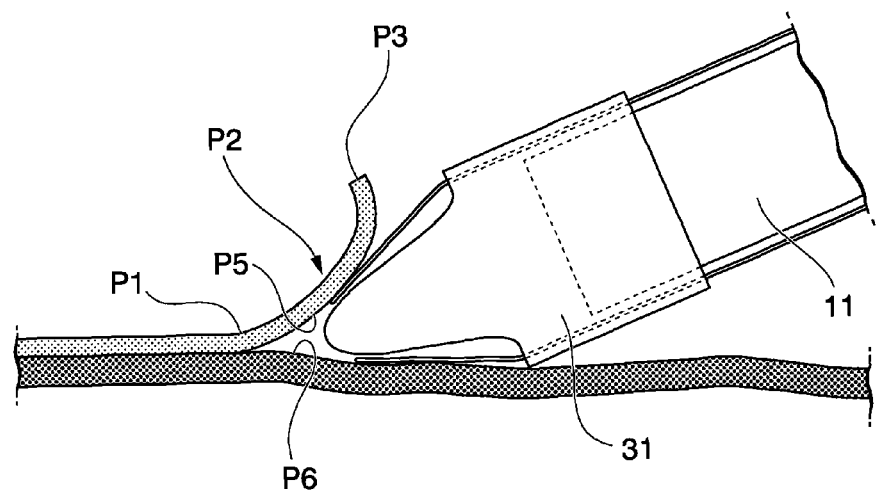
FIG. 14 is a view showing the operations of the first and third wires in the second modification of the first embodiment of the present invention.
Figure 15:
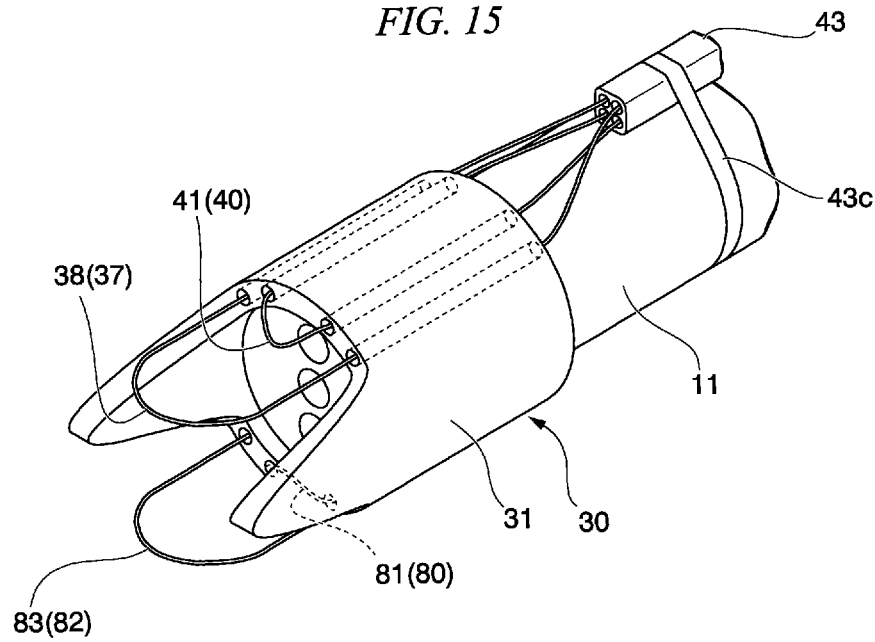
FIG. 15 is a perspective view showing operations of second and fourth wires in the second modification of the first embodiment of the present invention.
Figure 16:
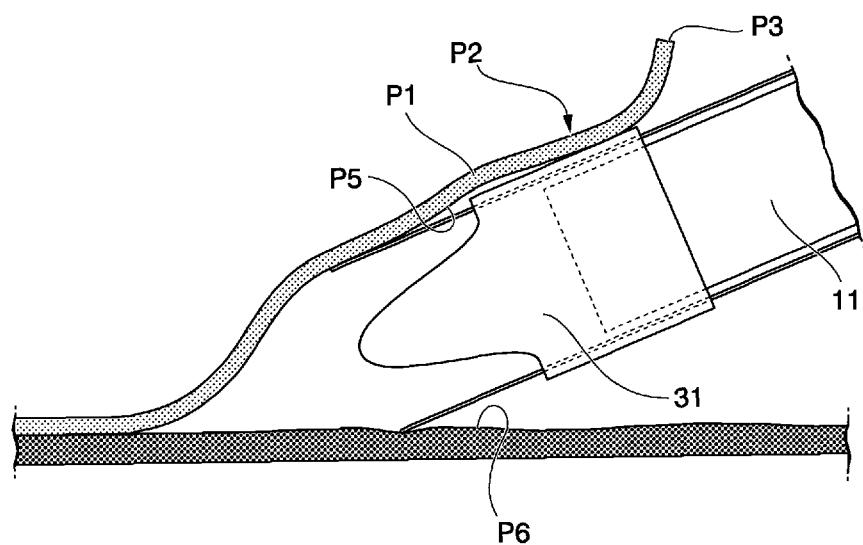
FIG. 16 is a view showing the operations of the second and fourth wires in the second modification of the first embodiment of the present invention.

FIGS. 13 and 14 are views showing operations of the first wire 37 and the third wire 80 in the present modification. FIGS. 15 and 16 are views showing operations of the second wire 40 and the fourth wire 82 in the present modification.

In the present modification, when the first wire 37 and the third wire 80 protrude from the cap 31 as shown in FIG. 13 and are used, the first wire 37 and the third wire 80 can be easily inserted into a gap between a submucosal layer P5 and a muscular layer P6 when a distal portion of the cap 31 begins to be inserted into an opening P3 as shown in FIG. 14.

The distal portion of the cap 31 is inserted between the submucosal layer P5 and the muscular layer P6, continues with incision, and is inserted between the submucosal layer P5 and the muscular layer P6. Then, as shown in FIG. 15, an operator stores the first wire 37 and the third wire 80, and also causes the second wire 40 and the fourth wire 82 to protrude to a distal side. In a state in which the second wire 40 and the fourth wire 82 protrude from a distal end to a distal side of the cap 31, as shown in FIG. 16, a distal end of the second U-shaped portion 41 and a distal end of the fourth U-shaped portion 83 spread the submucosal layer P5 and the muscular layer P6. For this reason, in comparison with when the submucosal layer P5 and the muscular layer P6 are widened using the first wire 37 and the third wire 80, the present modification is configured such that the submucosal layer P5 and the muscular layer P6 can be further widened.

The same effects as in the first modification are produced in the present modification. The third U-shaped portion 81 can prevent the muscular layer P6 from entering so deep as to obstruct the field of view of the endoscope device 10.

(Third Modification)

Figure 17:
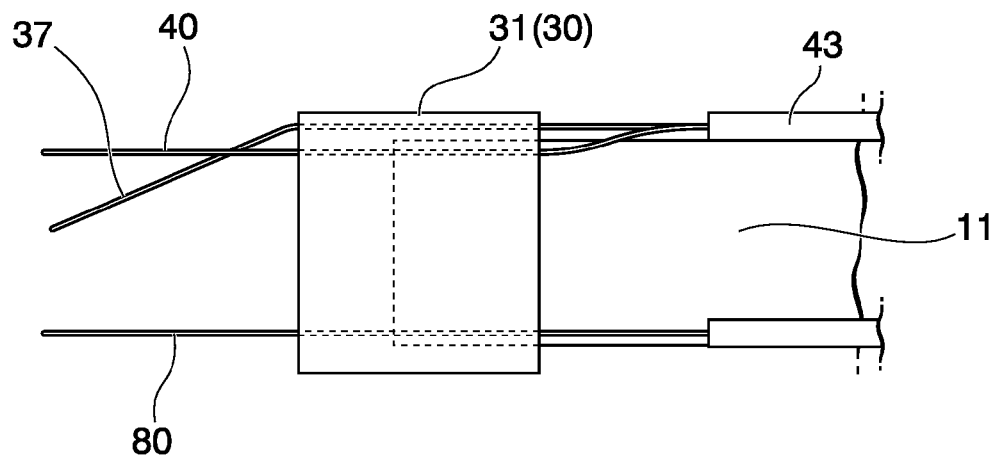
FIG. 17 is a side view showing a configuration of a third modification of the first embodiment of the present invention.
Figure 18:
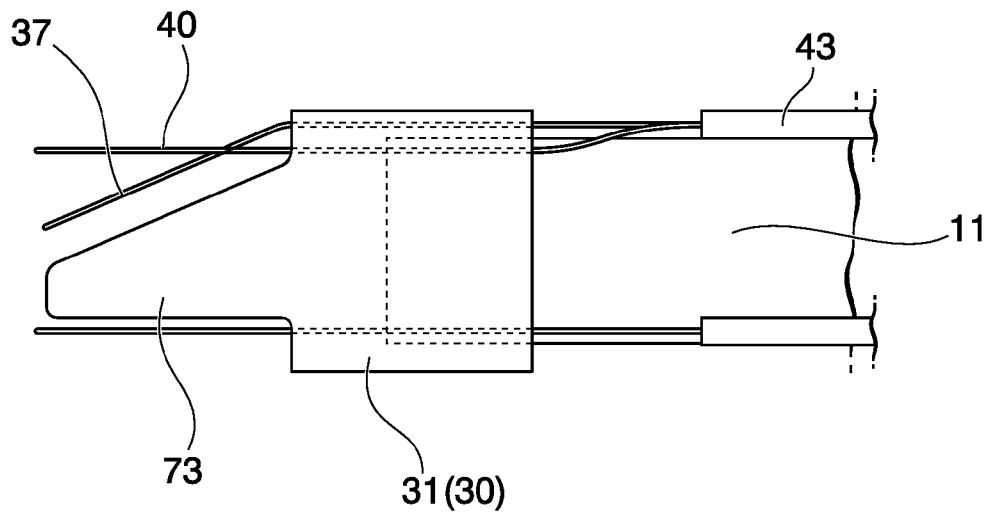
FIG. 18 is a side view showing another configuration example in the third modification of the first embodiment of the present invention.
Figure 19:
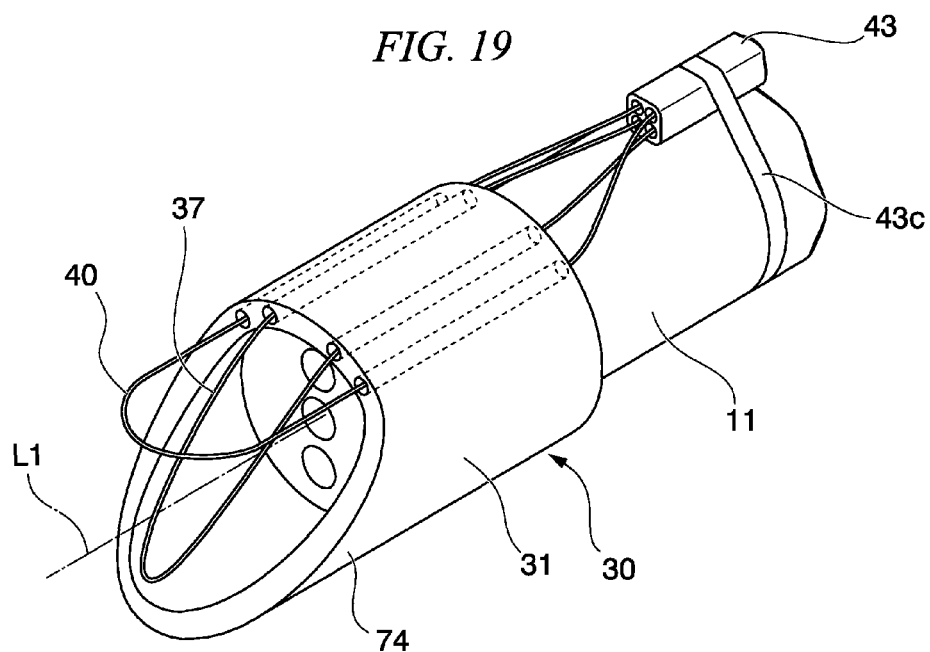
FIG. 19 is a perspective view showing yet another configuration example in the third modification of the first embodiment of the present invention.

Next, a third modification of the above-mentioned embodiment will be described. FIG. 17 is a side view showing a configuration of the present modification. FIG. 18 is a side view showing another configuration example in the present modification. FIG. 19 is a perspective view showing yet another configuration example in the present modification.

As shown in FIG. 17, in the present modification, a guide portion (a through-hole) for passing the fourth wire 80 described in the second modification is formed at the cap 31 described in the first embodiment.

In the present modification, a submucosal layer P5 and a muscular layer P6 are further spread using a fourth wire 80, compared to the first embodiment.

As shown in FIG. 18, the present modification may have projections 73 similar to the pair of projections 70 described in the first modification.

As shown in FIG. 19, instead of having a fourth wire 80, the present modification may have a projection 74 having an arc shape in a front view (when viewed in a direction of the central line L1 of the cap 31) and having an oblique surface perpendicular to the central line of the cap 31 in a side view (when viewed in a direction perpendicular to the central line L1 of the cap 31).

In the present modification, an operation site of an appropriate width can be secured when a wide operation site is required according to arrangement of a treatment tool channel of an endoscope device 10.

(Fourth Modification)

Figure 20:
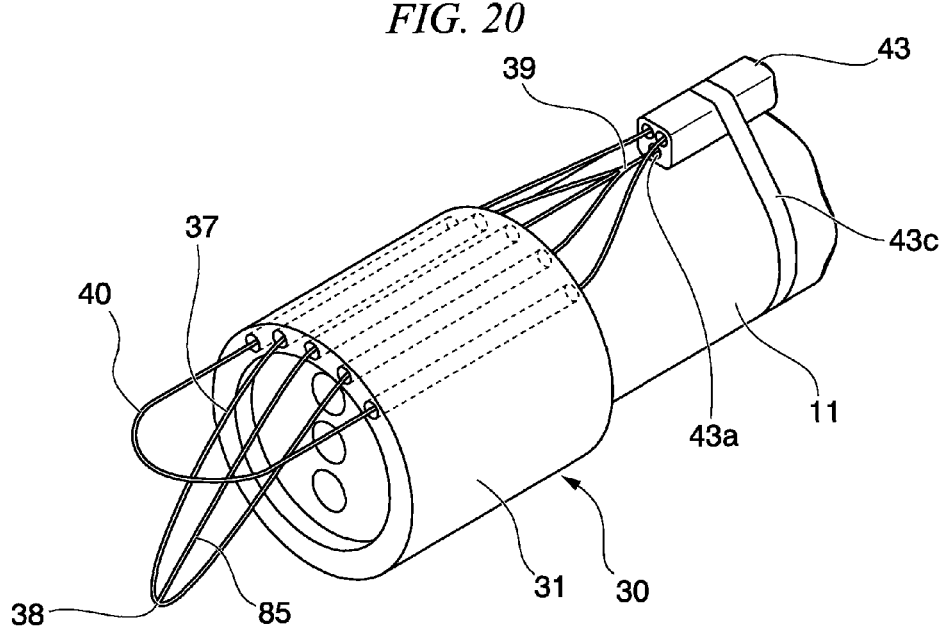
FIG. 20 is a perspective view showing a configuration of a fourth modification of the first embodiment of the present invention.

Next, a fourth modification of the above-mentioned embodiment will be described. FIG. 20 is a perspective view showing a configuration of the present modification. As shown in FIG. 20, in the present modification, a first wire 37 has a mucous membrane support 85 that is connected to a first U-shaped portion 38 and extends to a distal side. A through-hole for passing the mucous membrane support 85 is formed in a cap 31.

First proximal wire portions 39 of the first wire 37 are combined into one between a proximal end of the cap 31 and a distal end of a sheath portion 43. A proximal end of the mucous membrane support 85 is combined into one with the first proximal wire portions 39.

In the present modification, a first sheath portion 43a through which the first proximal wire portions 39 are inserted in the sheath portion 43 has one through-hole because the first proximal wire portions 39 are combined into one.

In the present modification, when a submucosal layer P5 (see FIG. 9) falls into an area in which the first wire 37 has a U shape, the mucous membrane support 85 supports the submucosal layer P5. For this reason, a wide operation site and a good field of view can be created between the submucosal layer P5 and a muscular layer P6.

In the present modification, since the submucosal layer P5 is supported by the mucous membrane support 85, the submucosal layer P5 does not easily enter a gap between wires constituting the first U-shaped portion 38, and a field of view based on an endoscope device 10 is widely secured.

(Fifth Modification)

Figure 21:
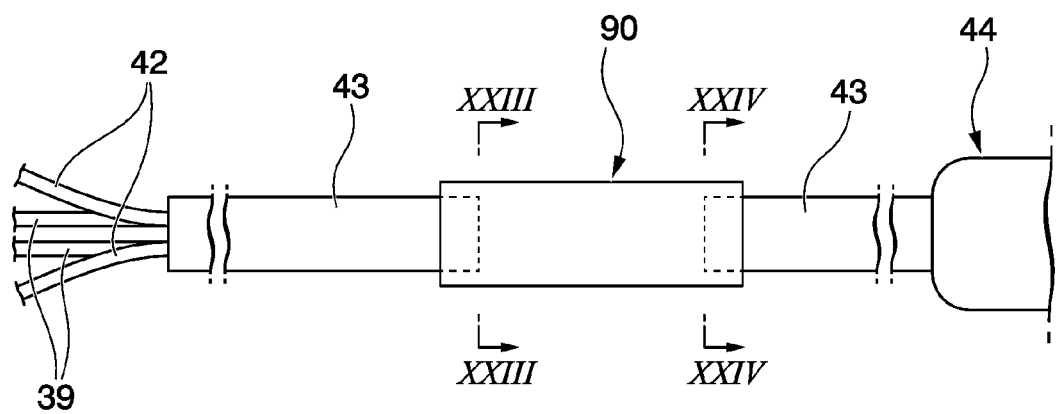
FIG. 21 is a top view showing a configuration of a fifth modification of the first embodiment of the present invention.
Figure 22:
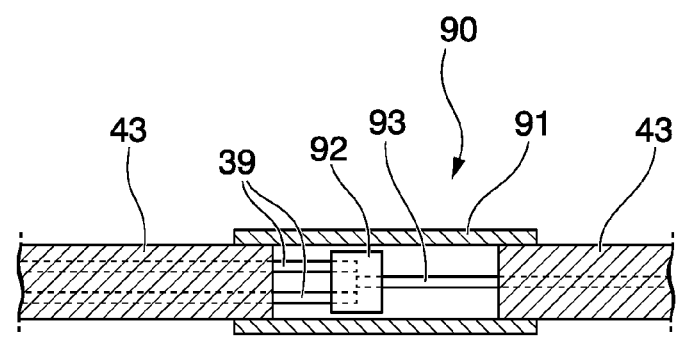
FIG. 22 is a cross-sectional view showing a sheath portion and a converter portion in the fifth modification of the first embodiment of the present invention by cutting the sheath and converter portions in a cross section passing the central lines thereof in a top view.
Figure 23:
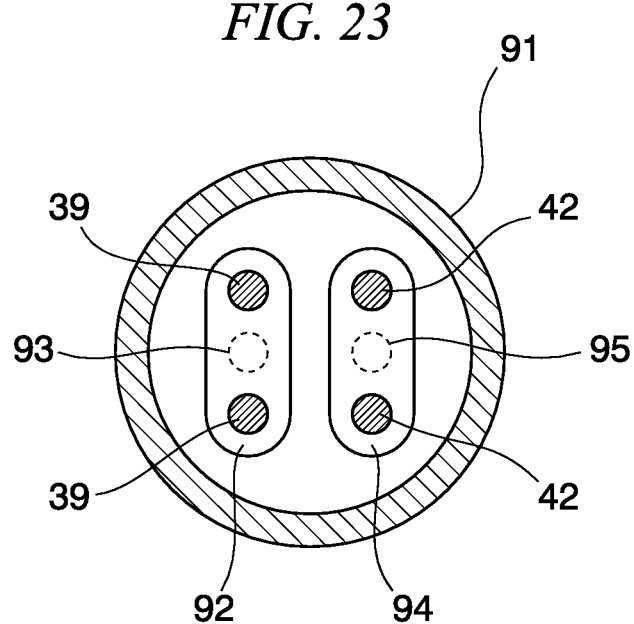
FIG. 23 is a cross-sectional view taken along line XXIII-XXIII of FIG. 21.
Figure 24:
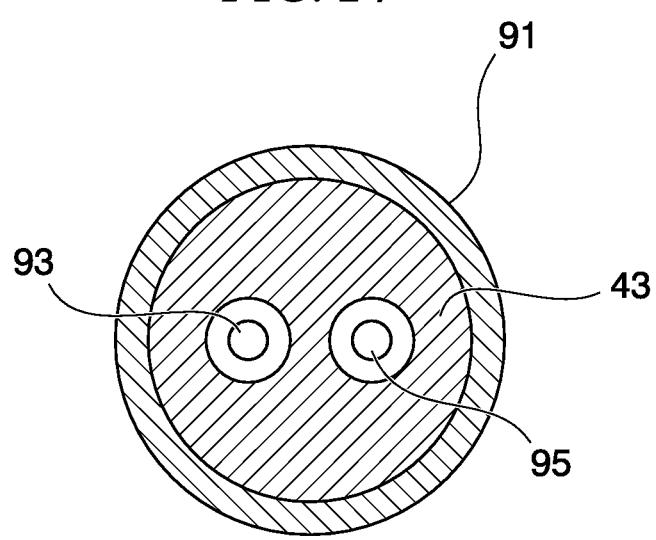
FIG. 24 is a cross-sectional view taken along line XXIV-XXIV of FIG. 21.
Figure 25:
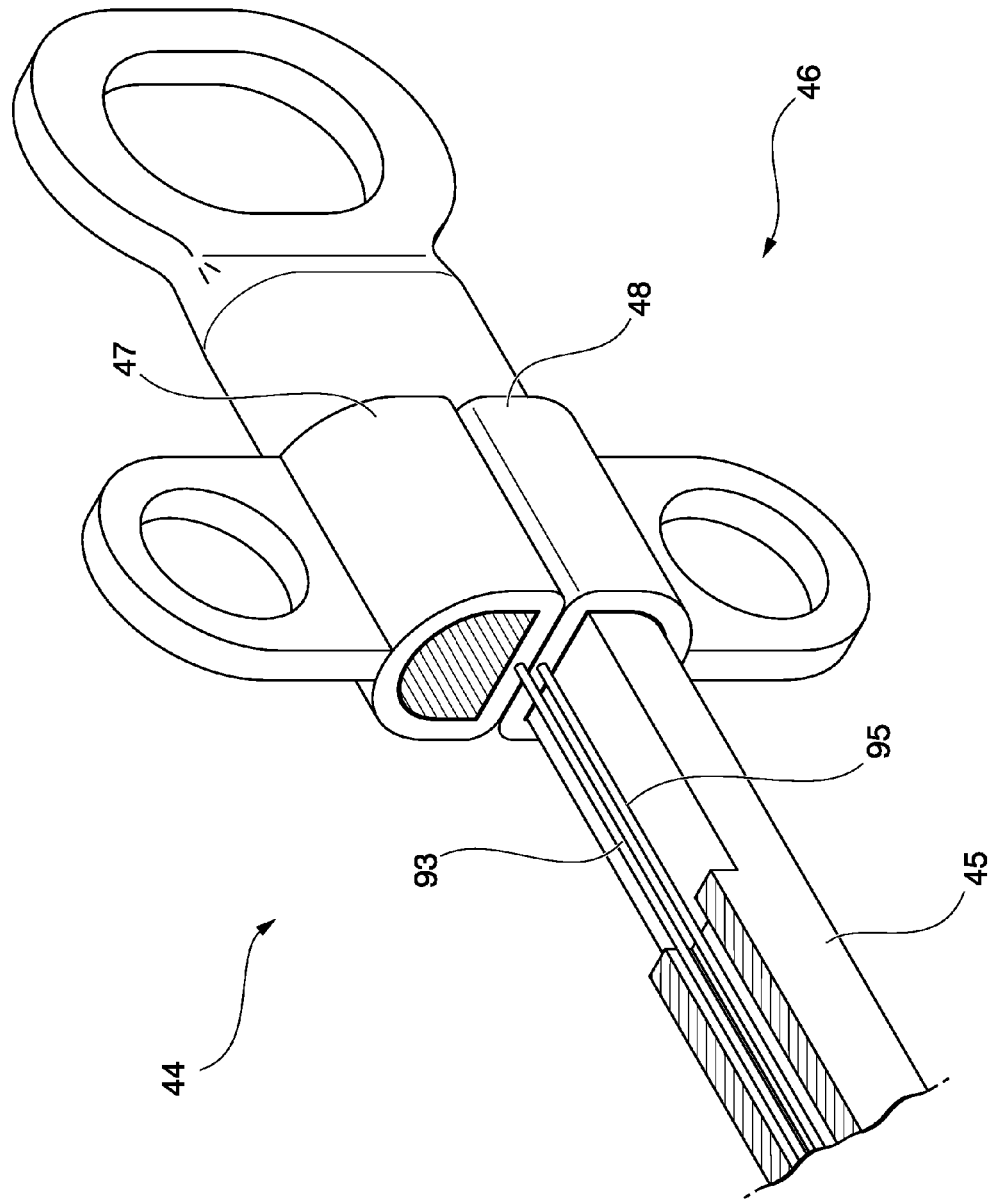
FIG. 25 is a perspective view showing a configuration of a manipulation portion in the fifth modification of the first embodiment of the present invention in a partial cross section.
Figure 26:
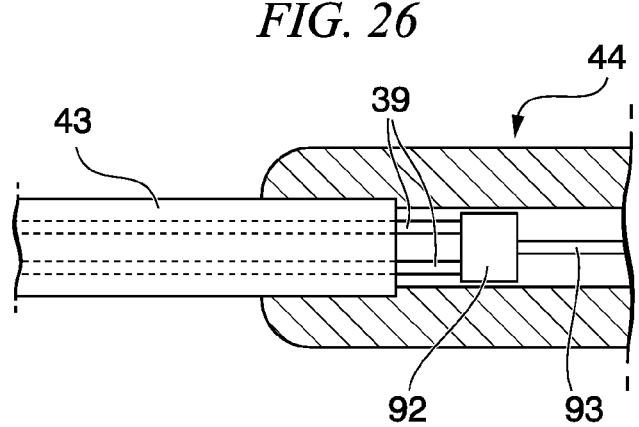
FIG. 26 is a view showing another configuration example of the fifth modification of the first embodiment of the present invention, and is a top view showing the manipulation portion in a partial cross section.

Next, a fifth modification of the above-mentioned embodiment will be described. FIG. 21 is a top view showing a configuration of the present modification. FIG. 22 is a cross-sectional view showing a sheath portion and a converter portion in the present modification by cutting them in a cross section passing the central lines thereof in a top view. FIG. 23 is a cross-sectional view taken along line XXIII-XXIII of FIG. 21. FIG. 24 is a cross-sectional view taken along line XXIV-XXIV of FIG. 21. FIG. 25 is a perspective view showing a configuration of a manipulation portion in the present modification in partial cross section. FIG. 26 is a view showing another configuration example of the present modification and is a top view showing the manipulation portion in a partial cross section.

As shown in FIGS. 21 to 24, in the present modification, a sheath portion 43 has a converter portion 90 that combines two first proximal wire portions 39 into one and two second proximal wire portions 42 into one.

The converter portion 90 is disposed at an intermediate portion of the sheath portion 43. The converter portion 90 has a tubular body 91, a first connector 92, and a second connector 94. The tubular body 91 is interposed at the intermediate portion of the sheath portion 43. The first connector 92 connects the first proximal wire portions 39 to a first connecting wire portion 93 (to be described below). The second connector 94 connects the second proximal wire portions 42 to a second connecting wire portion 95 (to be described below).

As shown in FIG. 25, the first connecting wire portion 93 and the second connecting wire portion 95 extend to a manipulation portion 44 through the inside of an area located at a proximal side of the converter portion 90 in the sheath portion 43. An area between the converter portion 90 and the manipulation portion 44 within the sheath portion 43 serves as a double lumen tube corresponding to the number of the first and second connecting wire portions 93 and 95.

In the manipulation portion 44, a proximal end of the first connecting wire portion 93 is fixed to a first slider 47, and a proximal end of the second connecting wire portion 95 is fixed to a second slider 48.

In the present modification, a quantity of force for manipulating a first wire 37 in the manipulation portion 44 is transmitted from the first slider 47 to the first wire 37 via the first connecting wire portion 93. On the other hand, a quantity of force for manipulating a second wire 40 in the manipulation portion 44 is transmitted from the second slider 48 to the second wire 40 via the second connecting wire portion 95.

In the present modification, the sheath portion 43 can be reduced in diameter in an area of a proximal side relative to the converter portion 90, compared to when four wires are laid from a distal end to a proximal end of the sheath portion 43.

Further, in the present modification, an improvement in flexibility of the sheath portion 43 is expected, compared to when the four wires are pulled around from the distal end to the proximal end of the sheath portion 43.

As shown in FIG. 26, the converter portion 90 may be provided for the manipulation portion 44.

(Sixth Modification)

Figure 27:
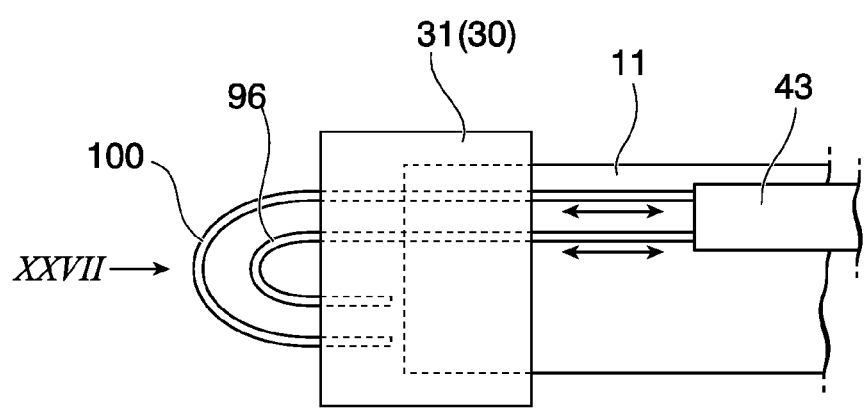
FIG. 27 is a top view showing a configuration of a sixth modification of the first embodiment of the present invention.
Figure 28:
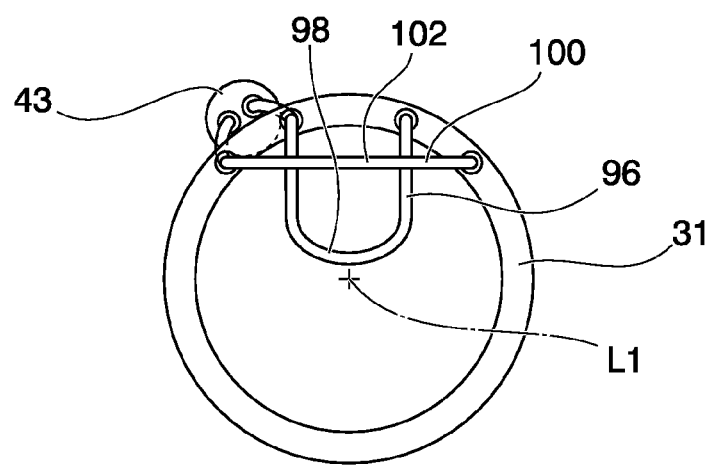
FIG. 28 is a front view of the present modification viewed in an XXVII direction in FIG. 27.

Next, a sixth modification of the above-mentioned embodiment will be described. FIG. 27 is a top view showing a configuration of the present modification. FIG. 28 is a front view of the present modification viewed in an XXVII direction in FIG. 27.

As shown FIGS. 27 and 28, in place of the first and second wires 37 and 40 described in the first embodiment, the present modification has first and second wires 96 and 100 having J shapes. The first wire 96 and the second wire 100 are preferably formed of a material having a high restoring force to a predetermined shape, like the first wire 37 and the second wire 40. For example, the first wire 96 and the second wire 100 are formed of a superelastic alloy, for instance, a NiTi alloy.

The sheath portion 43 is a double lumen tube. The sheath portion 43 corresponds to when the first wire 96 is one in a proximal side area of a cap 31 and the second wire 100 is one at the proximal side area of the cap 31 (see FIG. 27).

Of ends folded back in the J shape in the first wire 96, an end located at a distal side (a distal end 97 of the first wire 96) is fixed to the cap 31. The first wire 96 has a first U-shaped portion 98 bent at 180° with the same curvature as the first U-shaped portion 38 of the first wire 37 described in the first embodiment.

Of ends folded back in the J shape in the second wire 100, an end located at a distal side ((a distal end 101 of the second wire 100) is fixed to the cap 31. The second wire 100 has a second U-shaped portion 102 bent at 180° with the same curvature as the second U-shaped portion 41 of the second wire 40 described in the first embodiment.

As shown in FIG. 28, a positional relationship between the first wire 96 and the second wire 100 in a front view of the cap 31 (when viewed in a direction of the central line L1 of the cap 31) is the same as in the first embodiment.

In the present modification, in the first and second wires 96 and 100, respective wire portions extending toward a proximal side of an insertion portion 11 can be manipulated using the manipulation portion 44 (e.g., see FIG. 25). The same effects as in the first embodiment are produced in this configuration.

Like the fifth modification, a reduction in diameter and an improvement in flexibility of the sheath portion 43 are expected.

(Seventh Modification)

Figure 29:
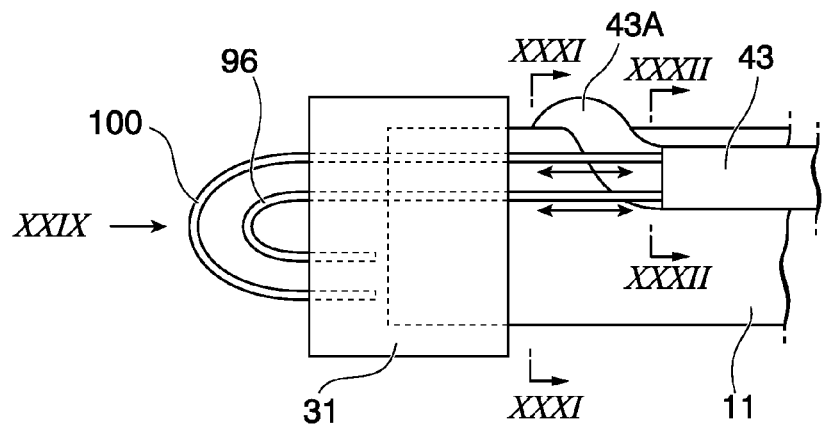
FIG. 29 is a top view showing a configuration of a seventh modification of the first embodiment of the present invention.
Figure 30:
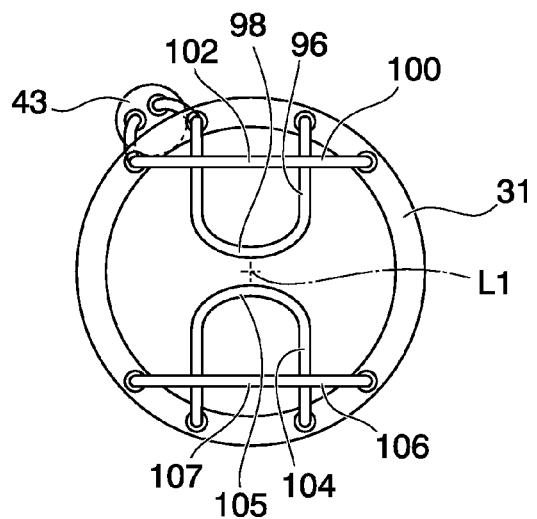
FIG. 30 is a front view of the present modification viewed in an XXIX direction in FIG. 29.
Figure 31:
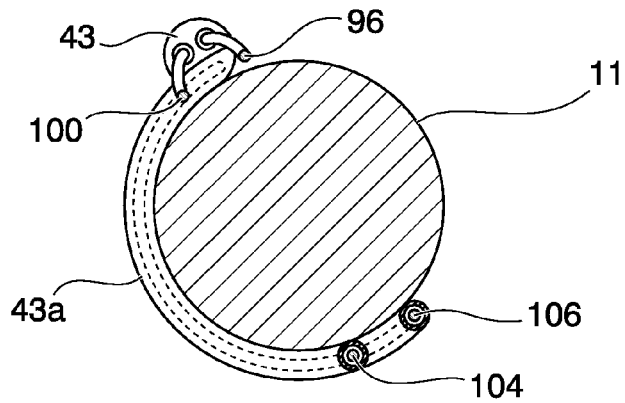
FIG. 31 is a cross-sectional view taken along line XXXI-XXXI of FIG. 29.
Figure 32:
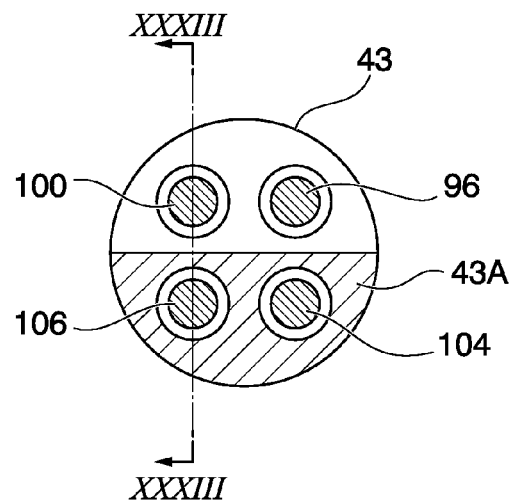
FIG. 32 is a cross-sectional view taken along line XXXII-XXXII of FIG. 29.
Figure 33:
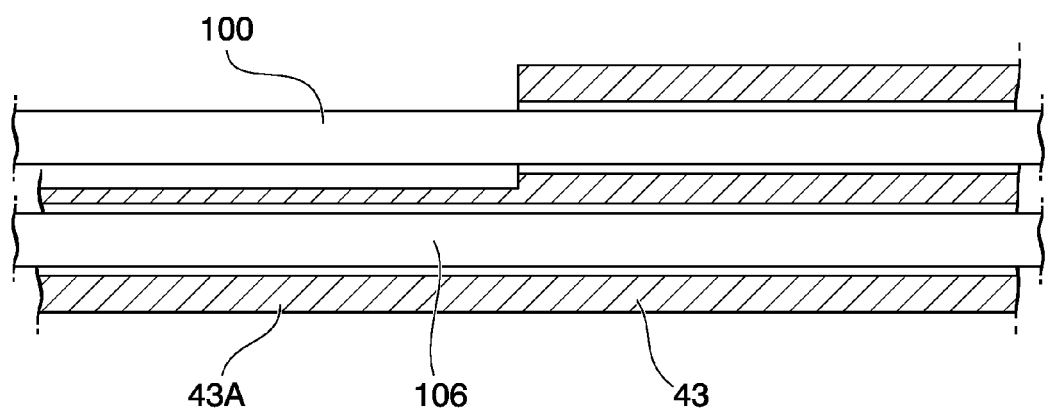
FIG. 33 is a cross-sectional view taken along line XXXIII-XXXIII of FIG. 32.

Next, a seventh modification of the above-mentioned embodiment will be described. FIG. 29 is a top view showing a configuration of the present modification. FIG. 30 is a front view of the present modification viewed in an XXIX direction in FIG. 29. FIG. 31 is a cross-sectional view taken along line XXXI-XXXI of FIG. 29. FIG. 32 is a cross-sectional view taken along line XXXII-XXXII of FIG. 29. FIG. 33 is a cross-sectional view taken along line XXXIII-XXXIII of FIG. 32.

As shown in FIGS. 29 to 33, in addition to the first and second wires 96 and 100 described in the sixth modification, the present modification has third and fourth wires 104 and 106 at positions at which the third and fourth wires 104 and 106 have rotational symmetry with an angle of 180° about the central line L1 of the cap 31 shown in FIG. 30 with respect to the first and second wires 96 and 100. Both the third wire 104 and the fourth wire 106 are preferably formed of a material having a high restoring force to a predetermined shape, like the first wire 37 and the second wire 40 described in the first embodiment. For example, the third wire 104 and the fourth wire 106 are formed of a superelastic alloy, for instance, a NiTi alloy.

The third wire 104 has rotational symmetry with an angle of 180° about the central line L1 of the cap 31 with respect to the first wire 96, and has a third U-shaped portion 105 bent at 180° with the same curvature as the first U-shaped portion 98 of the first wire 96.

The fourth wire 106 has rotational symmetry with an angle of 180° about the central line L1 of the cap 31 with respect to the second wire 100, and has a fourth U-shaped portion 107 bent at 180° with the same curvature as the second U-shaped portion 102 of the second wire 100.

A sheath portion 43 has an extension tube 43A. The extension tube 43A guides the third wire 104 and the fourth wire 106 to a position at which it has rotational symmetry with an angle of 180° about the central line L1 of the cap 31 with respect to the sheath portion 43. The extension tube 43A forms a distal portion of the sheath portion 43 along an outer surface of the insertion portion 11, and is fixed to a proximal end of the cap 31.

The sheath portion 43 is a multi-lumen tube. Four lumens of the sheath portion 43 are for insertion of the first wire 96, the second wire 100, the third wire 104, and the fourth wire 106. In the present modification, the converter portion 90 described in the fifth modification may be suitably applied.

The same effects as in the first embodiment are produced in this configuration.

Although an embodiment of the present invention has been described above in detail with reference to the drawings, the specific configuration is not limited to the embodiment, and also includes various modifications. The present invention is not limited to the aforementioned embodiment, but is only limited by the appended claims.

What is claimed is:

1. An endoscopic mucous membrane lifting instrument, comprising:
a cap mounted at a distal end of an insertion portion of an endoscope device, the insertion portion of the endoscope device having a longitudinal axis extending from a proximal end to a distal end;
a first wire disposed at the cap and configured to be capable of protruding from an outer circumferential portion of the distal end of the insertion portion, the first wire extending distal to the insertion portion and distally toward the longitudinal axis of the insertion portion;
a second wire disposed at the cap and be capable of protruding from the outer circumferential portion of the insertion portion, the second wire extending distal to the insertion portion and extending parallel to the longitudinal axis of the insertion portion; and
a wire-manipulating portion configured to independently operate the first wire and the second wire, wherein:
the first wire has a first U-shaped portion formed in a U shape at a distal end, and a first proximal wire portion that is connected with the first U-shaped portion and is connected to the wire-manipulating portion; and
the second wire has a second U-shaped portion formed in a U shape having a larger radius of curvature than that of the first U-shaped portion at a distal end, and a second proximal wire portion that is connected with the second U-shaped portion and is connected to the wire-manipulating portion.

2. The endoscopic mucous membrane lifting instrument according to claim 1, wherein:
the cap has a tubular portion that is mounted at the distal end of the insertion portion of the endoscope device, a first through-hole portion which is formed at an outer wall of the tubular portion to extend in parallel to the longitudinal axis of the insertion portion and into which the first wire is inserted, and a second through-hole portion which is formed at the outer wall of the tubular portion to extend in parallel to the longitudinal axis of the insertion portion and into which the second wire is inserted; and
the first wire has a first proximal wire portion that is manipulated by the wire-manipulating portion, and an oblique portion that is obliquely connected with the first proximal wire portion and is inclined to intersect with the extension line of the longitudinal axis of the insertion portion from a distal end of the first through-hole portion when protruding more distally from the distal end of the first through-hole portion.

3. An endoscopic treatment system for treating a living tissue, the endoscopic treatment system comprising:
the endoscopic mucous membrane lifting instrument according to claim 1;
the endoscope device having the insertion portion, the cap being capable of being mounted at the distal end of the insertion portion; and
a treatment tool mounted at the endoscope device and configured to perform treatment on a living tissue via the cap.

4. The endoscopic mucous membrane lifting instrument according to claim 1, wherein a distance between the first wire and the second wire is increased toward a distal side of the insertion portion, in a state in which the first wire and the second wire protrude from the outer circumferential portion of the insertion portion.

5. An endoscopic mucous membrane lifting instrument comprising:
a cap mounted at a distal end of an insertion portion of an endoscope device, the insertion portion of the endoscope device having a longitudinal axis extending from a proximal end to a distal end;
a first wire disposed at the cap and configured to be capable of protruding from an outer circumferential portion of the distal end of the insertion portion, the first wire extending distal to the insertion portion and distally toward the longitudinal axis of the insertion portion;
a second wire disposed at the cap and be capable of protruding from the outer circumferential portion of the insertion portion, the second wire extending distal to the insertion portion and extending parallel to the longitudinal axis of the insertion portion; and
a wire-manipulating portion configured to independently operate the first wire and the second wire, wherein:
the cap includes:
a projection portion formed to extend from the distal end of the insertion portion more distal than the insertion portion in the distal direction; and
a holder portion disposed at a position more proximal than a distal end of the projection and configured to hold the first wire and the second wire to project from and retract into the cap,
the projection portion includes:
a first projection portion configured to extend from the outer circumferential portion of the distal end of the insertion portion toward the distal direction more distal than the insertion portion; and
a second projection portion disposed at a position facing the first projection in a radial direction of the insertion portion and configured to extend from the outer circumferential portion of the distal end of the insertion portion toward the distal direction more distal than the insertion portion; and
the holder portion is disposed at a position between the first projection portion and the second projection portion in a radial direction of the outer circumferential portion of the distal end of the insertion portion.

6. The endoscopic mucous membrane lifting instrument according to claim 5, wherein:
the cap has a tubular portion that is mounted at the distal end of the insertion portion of the endoscope device, a first through-hole portion which is formed at an outer wall of the tubular portion to extend in parallel to the longitudinal axis of the insertion portion and into which the first wire is inserted, and a second through-hole portion which is formed at the outer wall of the tubular portion to extend in parallel to the longitudinal axis of the insertion portion and into which the second wire is inserted; and
the first wire has a first proximal wire portion that is manipulated by the wire-manipulating portion, and an oblique portion that is obliquely connected with the first proximal wire portion and is inclined to intersect with the extension line of the longitudinal axis of the insertion portion from a distal end of the first through-hole portion when protruding more distally from the distal end of the first through-hole portion.

7. An endoscopic treatment system for treating a living tissue, the endoscopic treatment system comprising:

the endoscopic mucous membrane lifting instrument according to claim 5;

the endoscope device having the insertion portion, the cap being capable of being mounted at the distal end of the insertion portion; and a treatment tool mounted at the endoscope device and configured to perform treatment on the living tissue via the cap.

8. The endoscopic mucous membrane lifting instrument according to claim 5, wherein a distance between the first wire and the second wire is increased toward a distal side of the insertion portion, in a state in which the first wire and the second wire protrude from the outer circumferential portion of the insertion portion.

9. An endoscopic mucous membrane lifting instrument, comprising:

a cap mounted at a distal end of an insertion portion of an endoscope device, the insertion portion of the endoscope device having a longitudinal axis extending from a proximal end to a distal end;

a first wire disposed at the cap and being configured to protrude from an outer circumferential portion of the distal end of the insertion portion, the first wire extending distally to the insertion portion and distally toward the longitudinal axis of the insertion portion, the first wire including:

a first U-shaped portion formed in a U shape at a distal end, and a first proximal wire portion connected to the first U-shaped portion and the wire-manipulating portion;

a second wire disposed at the cap and being configured to protrude from the outer circumferential portion of the insertion portion, the second wire extending distally to the insertion portion and extending parallel to the longitudinal axis of the insertion portion, the second wire including:

a second U-shaped portion formed in a U shape having a larger radius of curvature than that of the first U-shaped portion at a distal end, and a second proximal wire portion connected to the second U-shaped portion and the wire-manipulating portion; and a wire-manipulating portion configured to independently operate the first wire and the second wire.

10. The endoscopic mucous membrane lifting instrument according to claim 9, wherein:

the cap has a tubular portion that is mounted at the distal end of the insertion portion of the endoscope device, a first through-hole portion which is formed at an outer wall of the tubular portion to extend in parallel to the longitudinal axis of the insertion portion and into which the first wire is inserted, and a second through-hole portion which is formed at the outer wall of the tubular portion to extend in parallel to the longitudinal axis of the insertion portion and into which the second wire is inserted; and the first wire has a first proximal wire portion that is manipulated by the wire-manipulating portion, and an oblique portion that is obliquely connected with the first proximal wire portion and is inclined to intersect with the extension line of the longitudinal axis of the insertion portion from a distal end of the first through-hole portion when protruding more distally from the distal end of the first through-hole portion.

11. An endoscopic treatment system for treating a living tissue, the endoscopic treatment system comprising:

the endoscopic mucous membrane lifting instrument according to claim 9;

the endoscope device having the insertion portion, the cap being configured to connect to the distal end of the insertion portion; and a treatment tool mounted at the endoscope device and configured to perform treatment on the living tissue via the cap.

12. The endoscopic mucous membrane lifting instrument according to claim 9, wherein a distance between the first wire and the second wire is increased toward a distal side of the insertion portion, in a state in which the first wire and the second wire protrude from the outer circumferential portion of the insertion portion.

\* \* \* \* \*